(12) United States Patent
McClellan

(10) Patent No.: US 8,454,690 B2
(45) Date of Patent: Jun. 4, 2013

(54) SYSTEMS AND METHODS FOR TISSUE EXPANSION WITH FLUID DELIVERY AND DRAINAGE SYSTEM

(76) Inventor: William T. McClellan, Morgantown, WV (US)

(*) Notice: Subject to any disclaimer, the term of this patent is extended or adjusted under 35 U.S.C. 154(b) by 107 days.

(21) Appl. No.: 12/884,626

(22) Filed: Sep. 17, 2010

(65) Prior Publication Data
US 2011/0153017 A1 Jun. 23, 2011

Related U.S. Application Data

(60) Provisional application No. 61/289,381, filed on Dec. 22, 2009.

(51) Int. Cl.
*A61F 2/12* (2006.01)
*A61M 29/00* (2006.01)

(52) U.S. Cl.
USPC .......................................... 623/8; 604/103.02

(58) Field of Classification Search
USPC .......................................... 623/8; 604/103.02
See application file for complete search history.

(56) References Cited

U.S. PATENT DOCUMENTS

| | | | |
|---|---|---|---|
| 4,800,901 A | 1/1989 | Rosenberg |
| 5,630,843 A | 5/1997 | Rosenberg |
| 6,206,930 B1 | 3/2001 | Burg et al. |
| 6,567,219 B1 | 5/2003 | Tanaka |
| 6,592,625 B2 | 7/2003 | Cauthen |
| 6,619,291 B2 | 9/2003 | Hlavka et al. |
| 6,666,893 B2 | 12/2003 | Burg et al. |
| 6,718,985 B2 | 4/2004 | Hlavka et al. |
| 6,984,247 B2 | 1/2006 | Cauthen |
| 6,997,956 B2 | 2/2006 | Cauthen |
| 7,004,970 B2 | 2/2006 | Cauthen |
| 7,033,395 B2 | 4/2006 | Cauthen |
| 7,037,334 B1 | 5/2006 | Hlavka et al. |
| 7,052,516 B2 | 5/2006 | Cauthen, III et al. |
| 7,160,765 B2 | 1/2007 | Tanaka |
| 7,189,235 B2 | 3/2007 | Cauthen |
| 7,575,597 B2 | 8/2009 | Rehnke |
| 7,615,076 B2 | 11/2009 | Cauthen, III et al. |
| 7,670,379 B2 | 3/2010 | Cauthen |
| 7,670,380 B2 | 3/2010 | Cauthen, III |
| 7,749,273 B2 | 7/2010 | Cauthen, III et al. |
| 7,776,096 B2 | 8/2010 | Cauthen |
| 7,828,850 B2 | 11/2010 | Cauthen, III et al. |
| 7,846,208 B2 | 12/2010 | Cauthen, III et al. |
| 7,909,879 B2 | 3/2011 | Cauthen |
| 7,910,416 B2 | 3/2011 | Tanaka |
| 7,922,768 B2 | 4/2011 | Cauthen, III et al. |

(Continued)

OTHER PUBLICATIONS

International Search Report and Written Opinion dated Sep. 22, 2011 in corresponding PCT Application No. PCT/US10/61555.

*Primary Examiner* — Bruce E Snow
(74) *Attorney, Agent, or Firm* — Andrew D. Wright; Roberts Mlotkowski Safran & Cole, P.C.

(57) ABSTRACT

The invention provides systems and methods for tissue expansion. A tissue expander may have an implant portion which may be used to expand the tissue. A delivery/drainage system may be also be provided, which may be in fluid communication with a pocket surrounding the tissue expander. Various port configurations may be provided that may provide access to the implant portion and/or the delivery/drainage system. The tissue expander may advantageously help prevent or treat infection, or check the state of the pocket surrounding the tissue expander.

18 Claims, 24 Drawing Sheets

U.S. PATENT DOCUMENTS

| | | |
|---|---|---|
| 7,935,147 B2 | 5/2011 | Wales |
| 7,951,201 B2 | 5/2011 | Cauthen et al. |
| 7,963,992 B2 | 6/2011 | Cauthen, III et al. |
| 7,985,257 B2 | 7/2011 | Cauthen, III et al. |
| 7,993,405 B2 | 8/2011 | Cauthen, III et al. |
| 2002/0007218 A1 | 1/2002 | Cauthen |
| 2002/0111688 A1 | 8/2002 | Cauthen |
| 2002/0120337 A1 | 8/2002 | Cauthen |
| 2002/0123807 A1 | 9/2002 | Cauthen, III |
| 2002/0151980 A1 | 10/2002 | Cauthen |
| 2002/0156526 A1 | 10/2002 | Hlavka et al. |
| 2002/0177862 A1 | 11/2002 | Aranyi et al. |
| 2002/0189622 A1 | 12/2002 | Cauthen, III et al. |
| 2003/0120345 A1 | 6/2003 | Cauthen |
| 2003/0138999 A1 | 7/2003 | Tanaka |
| 2003/0153976 A1 | 8/2003 | Cauthen, III et al. |
| 2003/0158604 A1 | 8/2003 | Cauthen, III et al. |
| 2003/0163200 A1 | 8/2003 | Cauthen |
| 2003/0181983 A1 | 9/2003 | Cauthen |
| 2003/0187507 A1 | 10/2003 | Cauthen |
| 2003/0187508 A1 | 10/2003 | Cauthen |
| 2003/0220685 A1 | 11/2003 | Hlavka et al. |
| 2003/0220690 A1 | 11/2003 | Cauthen, III |
| 2003/0220693 A1 | 11/2003 | Cauthen, III |
| 2003/0220694 A1 | 11/2003 | Cauthen, III |
| 2004/0019378 A1 | 1/2004 | Hlavka et al. |
| 2005/0125011 A1 | 6/2005 | Spence et al. |
| 2005/0149197 A1 | 7/2005 | Cauthen |
| 2005/0222665 A1 | 10/2005 | Aranyi |
| 2005/0283246 A1 | 12/2005 | Cauthen, III et al. |
| 2006/0069429 A1 | 3/2006 | Spence et al. |
| 2006/0100711 A1 | 5/2006 | Cauthen |
| 2006/0129156 A1 | 6/2006 | Cauthen, III et al. |
| 2006/0129245 A1 | 6/2006 | Cauthen |
| 2006/0142864 A1 | 6/2006 | Cauthen |
| 2006/0161258 A1 | 7/2006 | Cauthen |
| 2006/0167553 A1 | 7/2006 | Cauthen, III et al. |
| 2006/0173545 A1 | 8/2006 | Cauthen, III et al. |
| 2006/0190085 A1 | 8/2006 | Cauthen |
| 2006/0206178 A1 | 9/2006 | Kim |
| 2006/0241773 A1 | 10/2006 | Cauthen |
| 2006/0287731 A1 | 12/2006 | Cauthen, III et al. |
| 2007/0061012 A1 | 3/2007 | Cauthen, III |
| 2007/0061013 A1 | 3/2007 | Cauthen, III et al. |
| 2007/0073407 A1 | 3/2007 | Cauthen, III et al. |
| 2007/0080188 A1 | 4/2007 | Spence et al. |
| 2007/0088438 A1 | 4/2007 | Cauthen, III et al. |
| 2007/0100348 A1 | 5/2007 | Cauthen, III et al. |
| 2007/0100354 A1 | 5/2007 | Cauthen, III et al. |
| 2007/0111549 A1 | 5/2007 | Tanaka |
| 2007/0156244 A1 | 7/2007 | Cauthen |
| 2007/0156245 A1 | 7/2007 | Cauthen, III et al. |
| 2007/0185497 A1 | 8/2007 | Cauthen et al. |
| 2007/0198021 A1 | 8/2007 | Wales |
| 2007/0233273 A1 | 10/2007 | Connell |
| 2007/0288041 A1 | 12/2007 | Cauthen |
| 2008/0033561 A1 | 2/2008 | Cauthen |
| 2009/0036989 A1 | 2/2009 | Cauthen, III et al. |
| 2009/0043343 A1 | 2/2009 | Wales |
| 2009/0157184 A1 | 6/2009 | Cauthen, III et al. |
| 2009/0259260 A1 | 10/2009 | Bentley et al. |
| 2010/0094425 A1 | 4/2010 | Bentley et al. |
| 2010/0324669 A1 | 12/2010 | Hlavka et al. |
| 2011/0082545 A1* | 4/2011 | Freund ............... 623/8 |

* cited by examiner

SYSTEMS AND METHODS FOR TISSUE EXPANSION WITH FLUID DELIVERY AND DRAINAGE SYSTEM

CROSS REFERENCE TO RELATED APPLICATIONS

This application claims priority under 35 U.S.C. §119 to U.S. Provisional Application No. 61/289,381 filed on Dec. 22, 2009, the contents of which are incorporated by reference herein in their entirety.

BACKGROUND OF THE INVENTION

1. Field of the Invention

The invention generally relates to medical devices and procedures, and more particularly to devices and methods for tissue expansion with fluid delivery and/or drainage.

2. Discussion of Background Information

Breast reconstruction with a tissue expander (TE) is currently the most common technique used for breast reconstruction. Typically immediately after the female has a mastectomy the reconstructive surgeon places a tissue expander which serves to stretch the skin and muscle in order to make room for a future implant or maintain the existing skin envelope. Skin sparing mastectomies are becoming the most common form of breast removal due to cancer, and it is advantageous to salvage this skin envelope. Newer techniques recently developed utilize allograft material, such as treated cadaveric dermis, to shield and hold the tissue expander in the pocket. Problems with the current technique are significant exposure of the patient to potential infection and seroma formation. Seroma is a benign collection of fluid which the body naturally makes following injury or surgery to fill an empty space. This fluid can make the skin turn red over the site where the seroma exists. Studies in plastic and reconstructive surgery have indicated that complications from seroma and/or infection affect 25% of all TE reconstructions.

Typically, when a subject (e.g., patient) develops a seroma, a medical practitioner sticks a large bore needle into the affected area of the subject and extracts the seroma fluid by sucking the fluid out with the needle. Such extraction often requires multiple aspirations. However, this extraction technique (e.g., puncturing with a needle) cannot safely be done with a traditional implanted tissue expander or implant (TE/implant device) because of the risk of puncturing the TE/implant device. If the TE/implant device is punctured, then another surgery would be performed to remove, and possibly exchange, the damaged TE/implant device. Such additional surgery is undesirable if the process that was originally being treated was a benign process, such as a seroma, since the patient would be exposed to undue anesthesia risk and additional infection risk when exchanging the TE/implant.

An infection associated with a TE/implant device also normally causes a reddening of the skin. The patient skin overlying the TE may also become reddened following TE placement and the beginning of placing (e.g., injecting) fluid percutaneously into the TE. Accordingly, a medical practitioner may have a difficult time differentiating between a seroma, an infection, and other common patient reactions. Unfortunately, a surgeon cannot stick a needle into the reddened area for fluid drainage and/or testing because, as already described, this may puncture and deflate the tissue expander if the tissue expander is accidentally stuck with the needle.

Using current methods, a TE that becomes infected must be removed, requiring the patient to undergo another general anesthesia and potentially lose the skin pocket which may have been created with expansion. Although a seroma and an infection have been described thus far as exclusive of one another, these events may be linked. For example, larger seromas often drain through the patient's skin causing an opening and exposing the TE to infection.

A tissue expansion device could also play a role in primary augmentation. Occasionally a primary breast augmentation implant will become infected. The capsule surrounding the TE is relatively avascular and the physician cannot treat infection within such a space. There is no current way to safely place antibiotics percutaneously into the space to fight infection. As such, current treatment involves unwanted additional surgery, such as removing the implant, washing out the pocket and then replacing a new implant over a drain.

More breast reconstructions are being performed with allograft, which has higher incidence of seroma and infection than traditional repair likely due to the fact that the artificial dermis is quite hydrophilic and attracts water around the implant. Also this results in two nonvascular components being next to one another, which increases the likelihood that one or both will become infected.

Thus, a need exists for improved systems and methods that may prevent or treat infections or seroma formations during tissue expansion.

SUMMARY OF THE INVENTION

The invention provides systems and methods for tissue expansion. Various aspects of the invention described herein may be applied to any of the particular applications set forth below or for any other types of tissue manipulation. The invention may be applied as a standalone system or method, or as part of integrated medical procedure, such as breast reconstruction. It shall be understood that different aspects of the invention can be appreciated individually, collectively, or in combination with each other.

A patient's body typically forms a capsule around an implant or tissue expander (TE). Such a capsule, defining a pocket, may be avascular. A tissue expander in accordance with aspects of the invention may be used to treat an infection with antibiotics even though there are few or no blood vessels in the pocket to deliver the antibiotics. In embodiments, a pocket port allows fluidic access to the space inside the capsule surrounding the tissue expander, e.g., the pocket.

When an implant infection occurs, the current gold standard is to remove the implant, wash out with antibiotic saline, and close over a drain. This is undesirable in the skin sparing mastectomy population because the soft pliable tissue envelope that the subject had following the mastectomy will be lost. However, an implant provided in accordance with embodiments of the invention may be placed as a space holder and treated with intrapocket antibiotics. As such, implementations of the invention allow a practitioner to wait until the infection resolves and then continue expansion and/or eventually replace with another implant. Implementations of the invention may save the patient from having to come to clinic repeatedly, e.g., every two weeks, for expansion once the skin has retracted.

Using a tissue expander in accordance with an embodiment of the invention may help eliminate biofilm formation on the implant surface. Bacteria are believed to live in complex communities called biofilms. These communities make it more difficult to treat infections of foreign material with antibiotics. In accordance with aspects of the invention, antibiotic or silver coated items are used to treat and prevent these biofilms in the area of tissue expanders.

For example, in accordance with an embodiment of the invention, a tissue expander may include antibiotic coating. This tissue expander may go beyond just simple coating. It may allow diagnostic and therapeutic maneuvers. In addition, the tissue expander may be coated with a dissolvable material that may slowly leach out antibiotics. In embodiments, the dissolving material disrupts biofilm formation since the surface that the biofilm is growing on is constantly eroding away.

Thus, a tissue expander in accordance with aspects of the invention may be provided to prevent, diagnose, and/or treat tissue expansion infection. In embodiments, the tissue expander may also allow drainage of periprosthetic fluid for culture and/or drainage of seroma or hematoma. In embodiments, the tissue expander may be used as either a primary tissue expander by replacing traditional expanders or used as a salvage implant or spacer once infection has taken place with a tissue expander or implant. A tissue expander in accordance with aspects of the invention can be used to hold the skin envelope following skin sparing mastectomy.

In accordance with a first aspects of the invention, there is a tissue expander comprising: an implant shell defining an internal cavity configured to contain a fluid; an implant port providing fluidic access to the internal cavity of the implant shell; a delivery system contacting the implant shell, wherein the delivery system is in fluidic communication with an area at an exterior of the tissue expander; and a pocket port providing fluidic access to the delivery system.

The delivery system may include a delivery canal encircling at least a portion of a circumference of the implant shell on a posterior side of the tissue expander. The delivery canal may comprise a plurality of openings that place an interior of the delivery canal in fluidic communication with the area at the exterior of the tissue expander. The delivery system, including the delivery canal, may be fluidically isolated from the internal cavity of the implant shell. The delivery system may further comprise an auxiliary delivery canal at an anterior side of the tissue expander, the auxiliary delivery canal comprising a plurality of holes, and the delivery canal and the auxiliary delivery canal being in fluidic communication. The delivery canal may be more rigid than the implant shell. The tissue expander may further comprise a communication channel connected to the pocket port and the delivery canal, wherein pocket port provides fluidic access to the delivery system via the communication channel.

In embodiments, the delivery system comprises a double-wall delivery region, the implant shell is a first wall of the double-wall delivery region, and a second wall of the double-wall delivery region comprises a plurality of holes that place an interior of the double-wall delivery region in fluidic communication with the area at the exterior of the tissue expander.

In embodiments, the implant port is integral to the implant shell. The pocket port may be integral to the implant shell. In particular embodiments, the implant port is integral to the implant shell and the pocket port is remote from the implant shell. In further embodiments, the implant port and the pocket port are contained together in a housing that is remote from the implant shell, the implant port is fluidically connected to the internal cavity by a first communication channel; and the pocket port is fluidically connected to a delivery canal of the delivery system by a second communication channel. In even further embodiments, the implant port and the pocket port are contained together in dual port that is integral with the implant shell.

The tissue expander may further comprise a coating on an exterior surface of the tissue expander. The coating is configured to dissolve inside a patient body.

In embodiments, the implant port provides selective fluidic access to the internal cavity for at least one of inflating and deflating the tissue expander. Moreover, the pocket port provides selective fluidic access to the delivery system for at least one of: injecting a fluid into the area at the exterior of the tissue expander, and extracting fluid from the area at the exterior of the tissue expander.

In accordance with another aspect of the invention, there is a tissue expander comprising: an implant shell defining an internal cavity configured to contain a fluid; an implant port providing fluidic access to the internal cavity for selectively inflating and deflating the implant shell; a delivery canal contacting at least a portion of the implant shell and comprising a plurality of openings that place an interior of the delivery canal in fluidic communication with an area at an exterior of the tissue expander; a communication channel connected to and in fluidic communication with the delivery canal; and a pocket port connected to and in fluidic communication with the communication channel. The implant port provides selective fluidic communication with the internal cavity exclusive of the delivery canal. The pocket port provides selective fluid communication with the delivery canal exclusive of the internal cavity.

In embodiments, the pocket port, the communication channel, and the delivery canal are configured for at least one of: injecting a fluid into the area at the exterior of the tissue expander, and extracting fluid from the area at the exterior of the tissue expander. The delivery canal may be more rigid than the implant shell.

In accordance with further aspects of the invention, there is a method for tissue expansion. The method includes: providing a first fluid via an implant port to an implant shell configured to contain the first fluid within, wherein the implant port is integral to the implant shell; and providing a second fluid via a pocket port to a delivery canal in contact with the implant shell, thereby causing the second fluid to extrude from the delivery canal to an area outside the implant shell. The implant shell may be comprised in a tissue expander that is implanted in a body, and the area outside the implant shell is a pocket formed by the body around the tissue expander.

Other advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein. A variety of changes and modifications can be made within the scope of the invention without departing from the spirit thereof.

BRIEF DESCRIPTION OF THE DRAWINGS

Novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF EMBODIMENTS OF THE INVENTION

While preferred embodiments of the invention are shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. The figures are described herein using reference numbers that are specific to each respective figure; however, it is understood that the features of any one or more figures may be used with the system shown in another figure.

The invention generally relates to medical devices and procedures, and more particularly to devices and methods for tissue expansion with fluid delivery and/or drainage. In accordance with aspects of the invention, a tissue expander comprises an implant shell, an internal cavity defined by an interior of the implant shell, and a channel (also referred to herein as a delivery canal) on an exterior of the implant shell. An access port (also referred to herein as an implant port) provides selective fluid communication with the internal cavity such that the implant shell may be inflated (or deflated) by introducing fluid into (or extracting fluid out of) the cavity. The tissue expander further comprises at least one channel arranged on an exterior of the implant shell. A pocket port provides selective fluid communication with the channel via a communication channel. In embodiments, the channel has a plurality of holes (e.g., apertures, bores, slits, etc.) that provide fluid communication between an interior of the channel and an exterior of the channel. In this manner, the pocket port, communication channel, and channel combine to provide a system for selectively introducing fluid to (or extracting fluid from) a pocket around the exterior of the implant shell in the patient's body. In embodiments, the access port does not communicate with the channel, and the pocket port does not communicate with the internal cavity, i.e., the channel and the internal cavity are fluidically isolated from one another. As such, in embodiments, the access port and pocket port comprise mutually exclusive ports for: (i) selectively controlling the inflation of the tissue expander and (ii) injecting/extracting fluid to/from the pocket, respectively.

Figure 1:
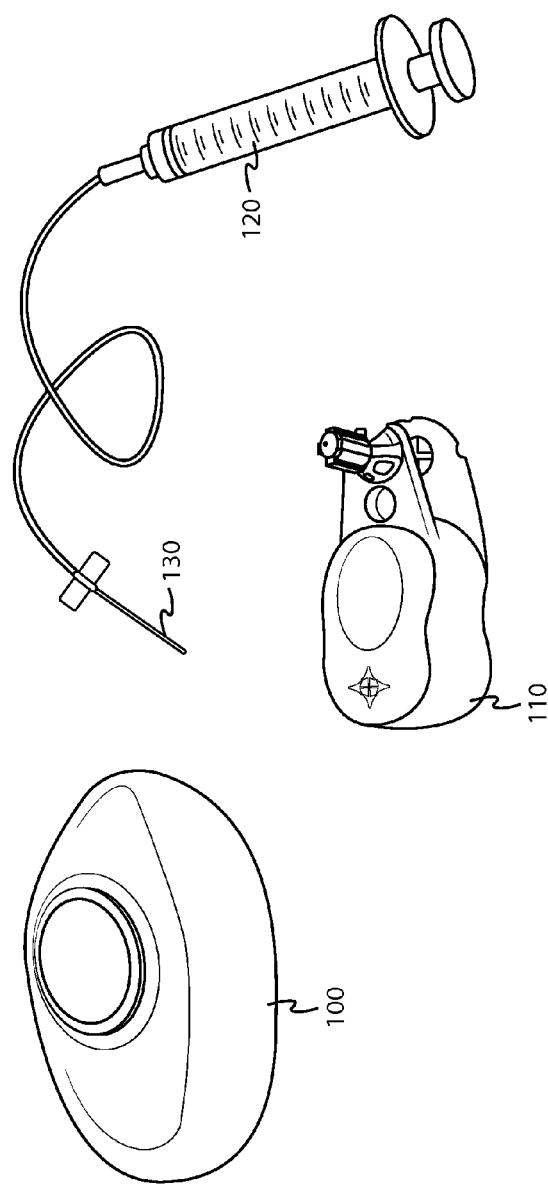
FIG. 1 shows a system used for tissue expansion, which may include a tissue expander, a magnet, and a fluid delivery system.

FIG. 1 shows a system used for tissue expansion, which may include a tissue expander 100, a magnet 110, and a fluid delivery system 120. The magnet 110 may be used to detect a particular portion of the tissue expander 100, such as an access port. The fluid delivery system 120 may include a needle 130 or other end used to access the interior of the tissue expander 100. The fluid delivery system 120 may provide a fluid to the interior (e.g., internal cavity) of the tissue expander 100 to cause the tissue expander 100 to expand. In some embodiments, the fluid delivery system 120 may also be used to access the interior of the tissue expander 100 to remove fluid from the tissue expander 100, which may cause the tissue expander 100 to contract or deflate.

Figure 2:
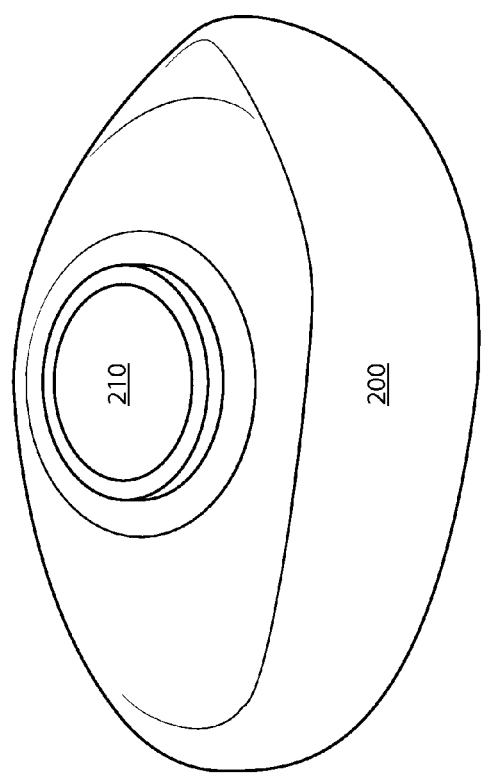
FIG. 2 shows an example of a tissue expander with an access port.

FIG. 2 shows an example of a tissue expander 200 with an access port 210. The access port 210 may be an integral port to access through the skin and instill saline or another fluid to cause tissue expansion. The tissue expander 200 may have a bit of fluid such as saline or air, or any other fluid within it to demonstrate how the tissue expander may be expanded. The tissue expander 200 may fill up like a balloon.

Figure 3:
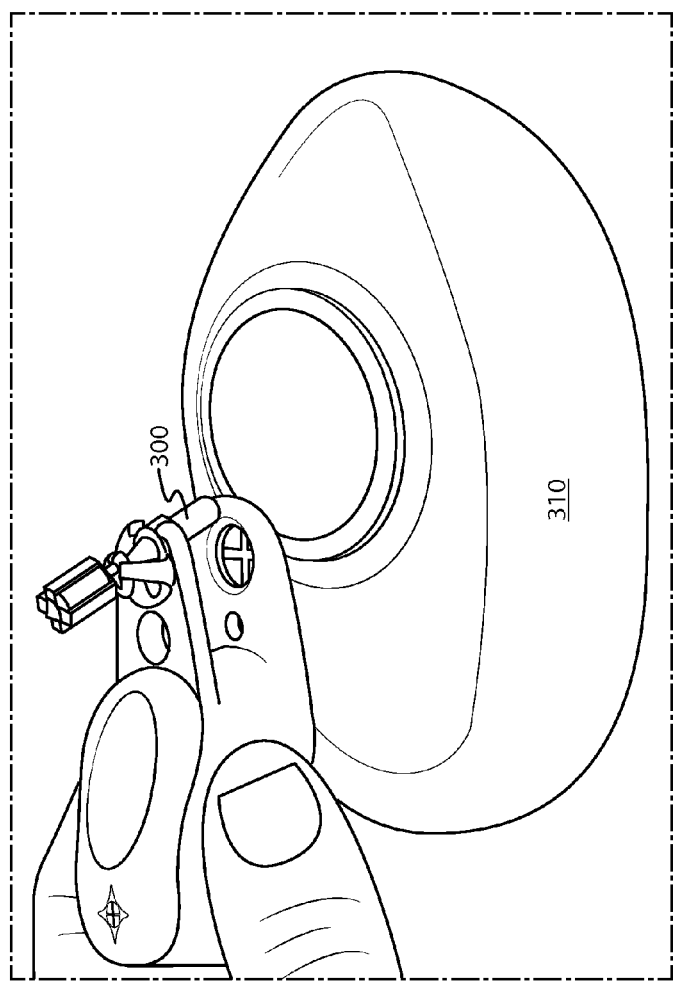
FIG. 3 shows a magnet running over a tissue expander.

FIG. 3 shows a magnet 300 running over a tissue expander 310. The tissue expander 310 may include a metal component that is attracted to or repulsed by the magnet 300. In this manner, running a magnet 300 over the tissue expander 310 may cause the metal component to move in response to the magnetic force. This may enable a practitioner to determine the location of the tissue expander 310 via the magnetic interaction between the magnet and the metal component even when the tissue expander 310 is implanted under the skin and not visible to the naked eye. The metal component may be provided in an access port (e.g., inflation/deflation port) of the tissue expander, or at any other suitable location on or in the tissue expander 310. Once the metal component is located using the magnet 300, the practitioner can stick an access needle through the skin to access the access port of the tissue expander 310.

Figure 4:
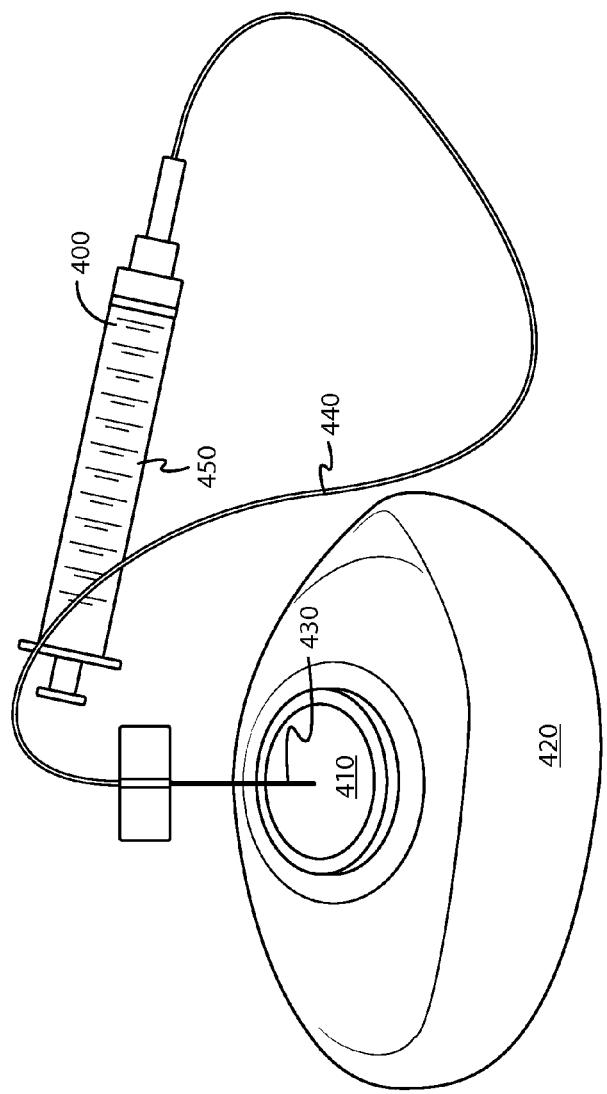
FIG. 4 shows an example of a fluid delivery system providing access to an access port of a tissue expander.

FIG. 4 shows an example of a fluid delivery system 400 providing access to an access port 410 of a tissue expander 420. The fluid delivery system 400 may include a needle 430 and a tube 440 to provide fluid to the interior of the tissue expander 420 via the access port 410 (e.g., inflation/deflation port). The needle may puncture the access port 410 to provide fluid to, or remove fluid from, the interior (e.g., internal cavity) of the tissue expander. The access port 410 may be provided with a self-healing/sealing material that, after being punctured by a needle of the fluid delivery system 400, reforms an airtight and liquid tight seal. In some instances, the fluid delivery system 400 may utilize a tip other than a needle that may be capable of delivering a fluid to, and removing fluid from, the tissue expander 420.

A pressure differential may be created to cause fluid to flow into or out of the tissue expander 420. For example, a positive pressure may be provided from outside the tissue expander 420, which positive pressure causes inflation of the tissue expander 420. In one example, a syringe 450 may be used to provide the positive pressure. In another example, a negative pressure may be provided from within the tissue expander 420 to draw fluid out of the tissue expander 420 for deflation of the tissue expander 420. Alternatively, pumps or valves may be utilized to assist with fluid flow.

Figure 5:
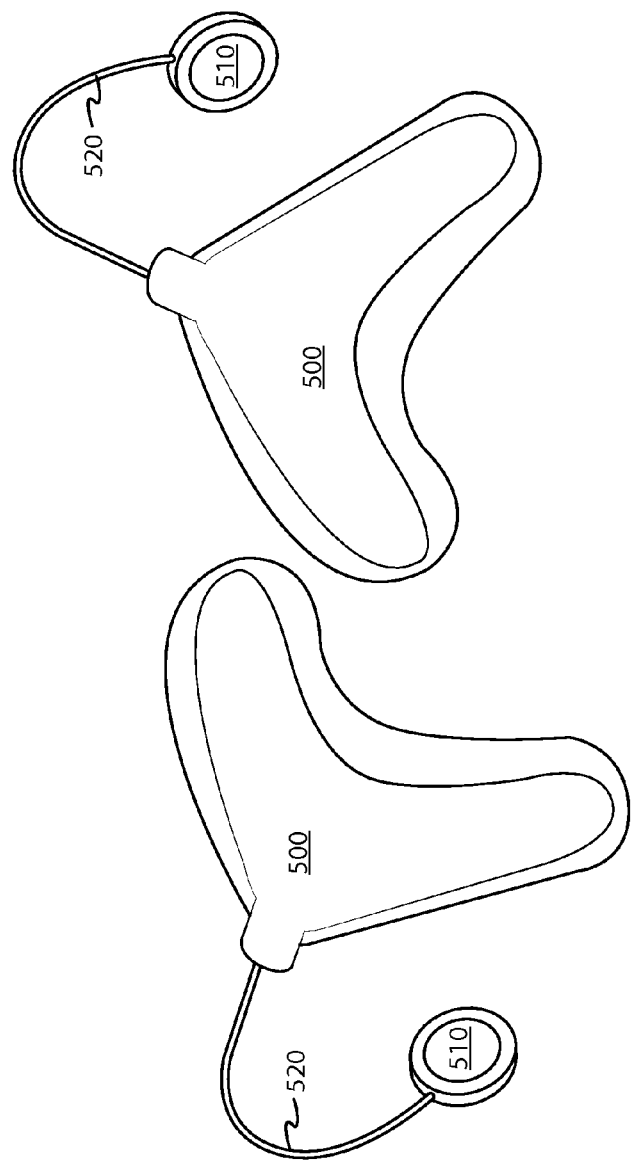
FIG. 5 shows examples of expansion devices with a remote port.

FIG. 5 shows examples of expansion devices 500 with a remote access port 510. For example, a scalp expansion device may be utilized. Any tissue expander may be used in accordance with the various embodiments of the invention. Such tissue expanders may include, but are not limited to, tissue expanders used for breast reconstruction, scalp expansion, face, neck, hands, arms, legs, or any other expansion of tissue which may or may not be the primary implant, or may be expanding tissue in preparation for a primary implant. Any discussion or illustration of a particular type of tissue expander herein may apply to any other type of tissue expander herein.

In some instances, the tissue expanders 500 may have a remote access port 510. The remote access port 510 may be used to provide a fluid to the tissue expander 500 in the manner already described herein, e.g., for inflation and/or deflation of the tissue expander 500. The remote access port 510 may be fluidically connected to the tissue expander 500 via a communication channel 520. The remote access port 510 may be located under the patient's skin or outside of the patient's skin. The features shown and described with respect to FIGS. 1-5 may be utilized in embodiments of the invention.

Tissue Expansion Device

Figure 6:
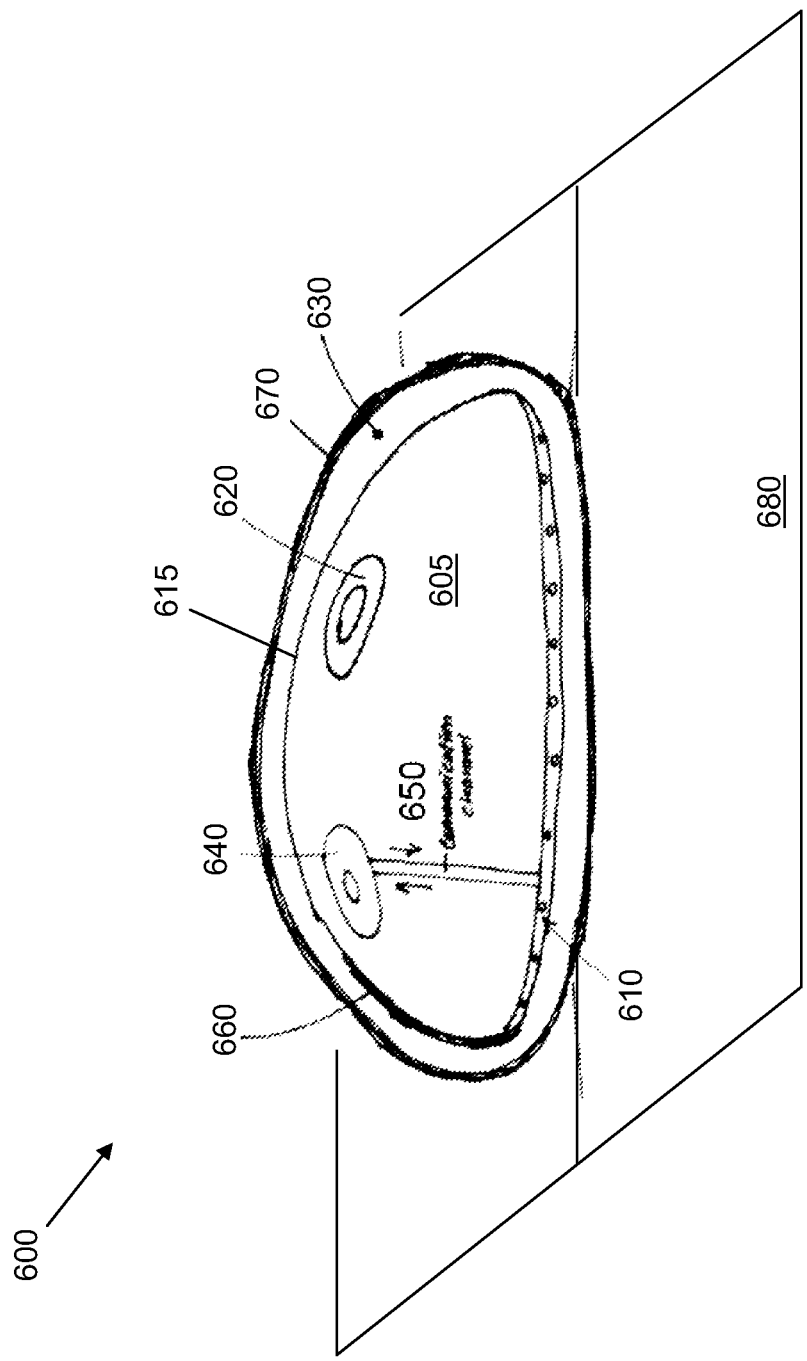
FIG. 6 provides an example of a tissue expander in accordance with an embodiment of the invention.

FIG. 6 provides an example of a tissue expander 600 in accordance with an embodiment of the invention. The tissue expander 600 may include an inside cavity 605 (e.g., internal cavity) and one or more channels 610 (also referred to herein as a delivery canal) around an implant shell 615. The inside cavity 605 may be defined by the implant shell 615. The implant shell 615 may be configured to contain a fluid within the inside cavity 605 in a fluid-tight manner, such that the tissue expander 600 may be inflated and deflated. The tissue expander 600 may include an implant port 620, which may be similar to access ports 210, 410, and 510 described herein. The implant port 620 may provide access to the inside cavity 605 of the implant and is where saline, water, air, or any other fluid, may be injected into or removed from the interior of the implant shell 615 for inflation and deflation of the tissue expander 600. Thus, an implant port 620 may provide fluidic access to the interior of the implant shell 615.

The implant shell 615 may have any shape and be composed of any suitable material in accordance with aspects of the invention. For example, the implant shell 615 may have a roughly spherical or hemispherical shape. Alternatively, the implant shell 615 may have an elongated shape. The implant shell 615 may also form various shapes that are suited for implanting into various locations of a subject's body. Such shapes may be designed to conform to a breast, scalp, face, neck, hands, arms, legs, or any other portion of a subject's body.

In embodiments, the one or more channels 610 about the implant shell 615 may provide a delivery/drainage system. Any discussion herein of a delivery/drainage system, channels, or canals may also apply to systems, channels, canals, or regions that may be used for delivery of a fluid and/or drainage/retrieval of a fluid. In embodiments, a delivery/drainage system may be connected to the implant shell 615. In some instances, the delivery/drainage system can be around the implant shell 615 or surround portions of the surface of the implant shell 615. The delivery/drainage system may leave at least a portion of the implant shell 615 exposed. Alternatively, the delivery/drainage system may substantially cover the entire exterior surface of the implant shell 615. The delivery/drainage system may be in fluidic communication with an exterior of the tissue expander 600 while not being in fluidic communication with the interior, e.g., inside cavity 605, of the implant shell 615 (i.e., the delivery system is fluidically isolated from the cavity defined within the implant shell).

As described herein, a pocket 630 is the space around a tissue expander 600 implant when the tissue expander 600 is implanted in a subject's body. The subject's body may form the pocket 630 as an area without blood vessels and, therefore, the pocket 630 may be isolated from antibiotics that are normally carried by the subject's vascular system.

In accordance with aspects of the invention, however, fluid communication with the pocket 630, or space or compartment around the tissue expander 600, may be provided via a percutaneous port such as a pocket port 640 and one or more channels 610 as described herein. In this manner, implementations of the invention may be used to deliver antibiotics, or any other fluids, to the pocket 630. Such communication may be provided for the drainage of any fluid within the pocket 630, or for the delivery of any fluid to the pocket 630. Devices in accordance with aspects of the invention may be adaptable to provide either or both of these functions.

The tissue expander 600 may also include a pocket port 640. In embodiments, the pocket port 640 may communicate with the channel(s) 610 around the implant shell 615. Thus, a pocket port 640 may provide fluidic access to a delivery/drainage system, which may include the channel(s) 610 and be in fluid communication with the pocket 630. The pocket port 640 can serve to deliver antibiotics or other fluids directly to the pocket 630 or it can be used to aspirate fluid from the pocket 630. In some instances, the pocket port 640 may be integral to the tissue expander 600, such as being formed integrally with the implant shell 615.

In some embodiments, at least one of the implant port 620 and pocket port 640 may comprise one or more remote ports. Exemplary remote ports are shown at reference numbers 755, 850, 1040, 1150, and others, as described in greater detail herein. A remote port may be separate from the implant shell 615 portion of the tissue expander 600. For example, a separate area may be created surgically for a remote port to rest in or on the subject body. The remote port may be connected to the tissue expander 600 by a tubing system. In some embodiments, a tissue expansion system can have one or two remote ports fluidly connected to the inside cavity 605 of the shell 615 and/or to the channel system 610. The remote port can be disengaged (pulled out) when it is desirable to keep the tissue expander implanted in the patient for a long time and take out the port through a separate small incision.

An implant port 620 may be an integrated in the implant shell 615 of the tissue expander 600, or a remote port may be provided that provides the same function as the implant port

620. Similarly, a pocket port 640 may be integrated in the implant shell 615 of the tissue expander 600, or a remote port may be provided that provides the same function as the pocket port 640. Any number of additional ports may be provided which may be integral to the tissue expander or which may be provided as a remote port.

The tissue expander may have a channel system 610 (also called a channel or delivery canal) in accordance with embodiments of the invention. In some embodiments, the channel system 610 may include a french drain type tubing system that can be integral and tightly bound to the implant shell 615 of the tissue expander 600. The channel system 610 can be located anywhere and in any configuration on the implant shell 615 of the tissue expander 600. In some instances, the channel system 610 may be located anywhere on the tissue expander 600 implant. However, in some instances, it may be preferable to provide the channel system 610 on the posterior surface of the implant shell 615, with respect to the orientation of the tissue expander 600 within the subject's body, because when a subject lies in a supine position, the fluid may move dependently posterior due to gravity. In other instances, the channel system 610 may be provided on an anterior surface and/or along the sides of the implant shell 615.

In embodiments, the channel system 610 can be used to deliver antibiotics or other chemicals to a pocket 630 which forms around the tissue expander 600 (e.g., around the implant). The channel system 610 can also "suck up" fluid which lies around the implant to be sent for culture or just aspirate sterile fluid. The channel system 610 can have a variety of configurations. In some embodiments, the channel system 610 may have a relatively more rigid structure to it than the implant shell 615 because it may be desirable to prevent collapse of the channel system 610 under pressure of injection or aspiration.

In some embodiments, one or more communication channels 650 may be provided between the channel system 610 and a pocket port 640 (whether integral or remote). The communication channel 650 may be fluidically connected to both the channel system 610 and the pocket port 640 to enable fluid to flow to or from the channel system 610 from the pocket port 640.

As described in greater detail herein, one or more stability tabs may be provided to a tissue expander 600 in embodiments of the invention. The stability tab can either be sewn down or can be a solid structure extending like a training wheel from the implant shell and which may serve to prevent the implant from being turned over or accidentally flipping over during normal use.

A tissue expansion device may also have an outside covering 660 arranged on an outer surface of the implant shell 615. The outside covering 660 of the tissue expander 600 implant may be composed of an integral substance that dissolves over time and exposes the outer surface of the implant shell 615 over time. This may help prevent biofilms from persisting on the tissue expander 600. Biofilms are a community of bacteria which are very hard to treat. Bacteria exist on the surface of the implant and often establish these communities when the implant is initially placed, and there may be small colonies of bacterial contamination. In some embodiments, the outside covering 660 of the tissue expander 600 implant may be a bonded dissolvable material with or without antibiotics, silver, or another metal. The outside covering may still remain soft.

In embodiments, the outside covering 660 comprises a dissolving material, such as polydioxanone (PDS). The dissolving material of the outside covering 660 helps prevent the formation of biofilms on the exterior surface of the tissue expander 600. As the outside covering 660 dissolves, the material on which the biofilm is formed collapses, thereby helping eliminate the biofilm.

In accordance with aspects of the invention, a tissue expansion system such as tissue expander 600 may be provided within a capsule 670. As described herein, a capsule 670 is a fibrous shell that the subject's body forms around an implant placed in the body. The implant shell 615 and capsule 670 are separate entities and there is a potential space, such as pocket 630, between them. The capsule 670 has very limited blood supply and usually has a smooth tough surface. The capsule 670 may form a physical barrier from the subject's body, vascular system, and immune system, and may serve as the boundary of a pocket 630.

In some embodiments, a tissue expander 600 may be positioned adjacent to, or in the proximity of, a firm area 680 such as, for example, a chest wall, skull, or any other bodily support structure or firm area from which to expand skin. In some embodiments, a posterior side of the tissue expander 600 may be the side of the tissue expander 600 located more closely to the firm area 680. An anterior side of the tissue expander 600 may be the side of the tissue expander located opposite the posterior side, and away from the firm area 680. In some instances, a tissue expander 600 is not positioned adjacent to a firm area 680. In such situations, the anterior side of the tissue expander 600 may be the side that is closer to the skin of the subject, while the posterior side may be the side deeper within the subject.

Thus, in accordance with aspects of the invention and as described herein, a tissue expander 600 comprises an implant shell 615, an internal cavity 605 defined by an interior of the implant shell 615, and a channel 610 on an exterior portion of the implant shell 615. An access port 620 provides selective fluid communication with the cavity 605 such that the implant shell 615 may be inflated (or deflated) by introducing fluid into (or extracting fluid out of) the cavity 605. The tissue expander 600 further comprises at least one channel 610 arranged on an exterior portion of the implant shell 615. A pocket port 640 provides selective fluid communication with the channel 610 via a communication channel 650. In embodiments, the channel 610 has a plurality of holes (e.g., apertures, bores, slits, etc.) that provide fluid communication between an interior of the channel 610 and an exterior of the channel 610. In this manner, the pocket port 640, communication channel 650, and channel 610 provide a system for selectively introducing fluid to (or extracting fluid from) the pocket 630 around the exterior of the implant shell 615 in the patient's body. In embodiments, the access port 620 does not communicate with the channel 610, and the pocket port 640 does not communicate with the cavity 605. As such, in embodiments, the access port 620 and pocket port 640 comprise mutually exclusive ports for: (i) selectively controlling the inflation/deflation of the tissue expander 600 and (ii) injecting/extracting fluid to/from the pocket 630, respectively.

Delivery/Drainage System

In accordance with an aspect of the invention, a tissue expander may include one or more inside cavities defined by a tissue expander shell and a surrounding channel system. The tissue expander may be incorporate features, components, or characteristics of other implants such as those described in: U.S. Pat. No. 5,630,843; U.S. Pat. No. 4,800,901; U.S. Patent Publication No. 2007/0233273; U.S. Pat. No. 6,666,893; U.S. Pat. No. 6,206,930; U.S. Pat. No. 7,575,597, the disclosures of all of which are incorporated by reference herein in their entirety.

In some embodiments, one, two, three, or more inside cavities, such as cavity 605, may be provided in a tissue expander in accordance with aspects of the invention. The inside cavities may be filled with a fluid such as saline, water, or air. When a plurality of cavities are provided, they may or may not be in fluid communication with one another. The inside cavities may be filled with fluid, causing them to expand, and expand surrounding tissue.

The cavities may all be filled with the same type of fluid, or different fluids. They may be filled to the same or differing degrees of internal pressure and/or volume. A tissue expander shell or shells defining one or more cavities can have varying shapes or sizes. Such shapes or sizes may reflect where the tissue expansion device is being deployed within a subject's body.

A channel system, such as channel 610, may surround the one or more inside cavities. The channel system may have any shape or configuration. For example, one, two, three, four, five, six, or more channels may be provided, which may surround the inside cavity. In other embodiments, the channel system may include sacs, regions, or outside layers that may surround the inside cavities. Any of the channels, sacs, regions, and/or layers of the channel system may be provided anywhere around the inside cavity, such as on or near the posterior side, the anterior side, and/or a lateral side. A part of a tissue expander shell may or may not be exposed and remain uncovered by the channel system. In some instances, a majority of the shell surface may remain uncovered by a channel system.

Figure 7:
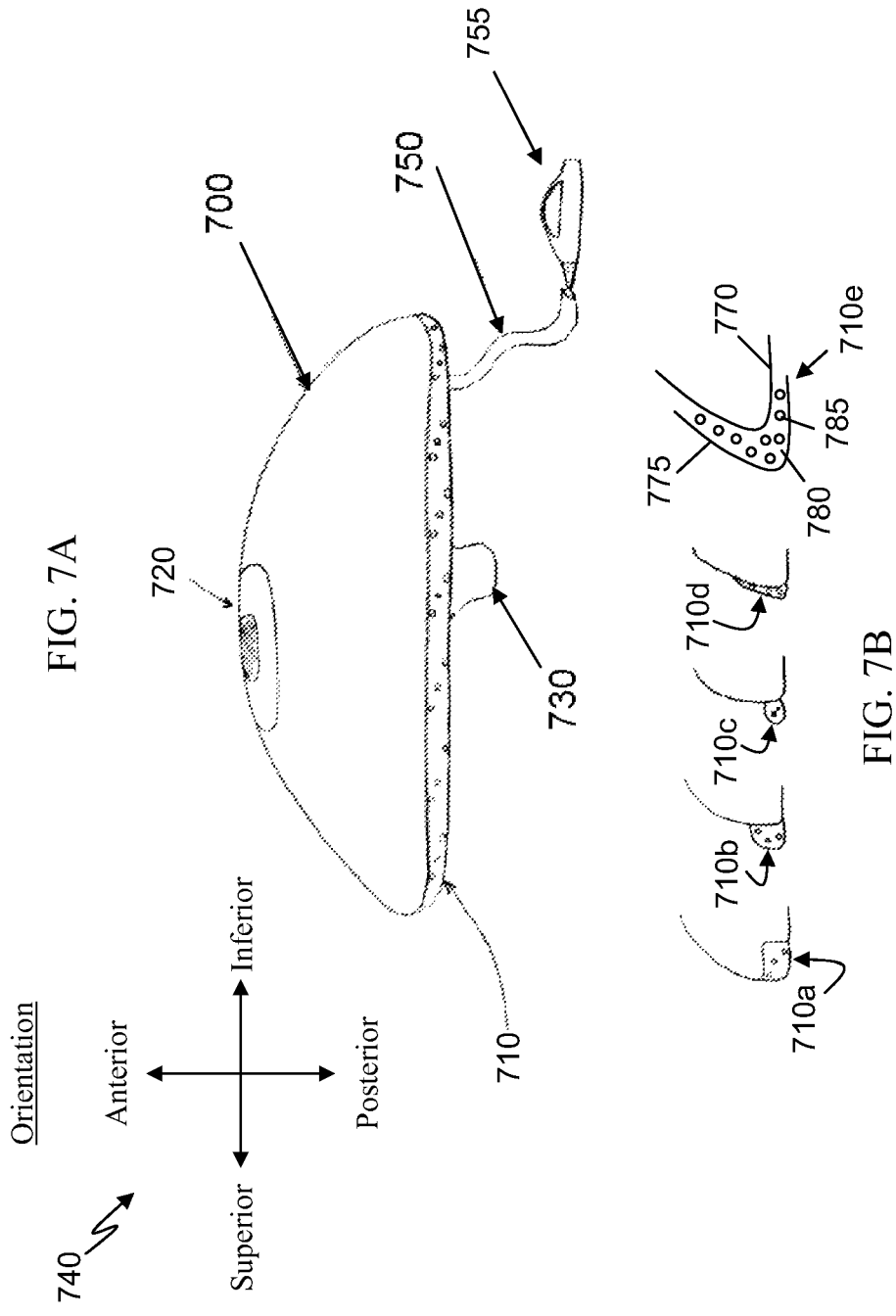
FIGS. 7A and 7B show a tissue expander with a delivery canal in accordance with aspects of the invention.

FIG. 7A shows a tissue expander 700 with a delivery canal 710. The tissue expander 700 may include an access port 720 (also referred to herein as an implant port), which may be similar to access port 620, that may be integral to the tissue expander. The access port 720 may allow fluid to be delivered to an inside cavity of the tissue expander 700. In some embodiments, the tissue expander 700 may also have an external coating. In one example, the external coating may be an antimicrobial coating. A tissue expander 700 may have one, two, three, four, or more stability tabs 730. The stability tabs 730 may be placed near a posterior side of the tissue expander 700.

In one embodiment, a delivery canal 710, which may be similar to channel 610, may be provided around a posterior 740 side of a tissue expander 700. The delivery canal 710 may be in fluid communication with a communication channel 750, which may be similar to communication channel 650. The communication channel 750 may be connected to a remote pocket port 755, which may be similar in function to pocket port 640. In other instances, the delivery canal 710 may be in fluid communication with an integral pocket port via a communication channel.

According to aspects of the invention, the delivery canal 710 may be integrated in various ways around the tissue expander. FIG. 7B depicts several exemplary delivery canals 710a-e showing how the delivery canal may be integrated into the tissue expander so that it protrudes or does not protrude from the tissue expander. In some instances, the delivery canal may go around the posterior circumference of the tissue expander. The delivery canal may be provided over the exterior surface of the implant shell. This may cause the delivery canal to have a profile that extends outward from the implant shell, such as shown at 710b, 710c, and 710d. In other embodiments, the delivery canal may be provided within the perimeter of the implant shell, as shown at 710a, which may cause the profile of the inside cavity to be smooth, so that the delivery canal does not extend outwards on the surface. A delivery canal may or may not protrude from a surface on an exterior or interior side to any degree.

In a particular embodiment of the invention, the delivery canal 710e may be provided as a double-walled portion of the shell of the tissue expander. For example, the tissue expander may comprise a first shell 770, which may be similar to shell 615, that defines an internal inflatable cavity of the tissue expander. The tissue expander may further comprise a second shell 775 extending around a substantially entirety of the first shell 770 in a double-wall fashion, with a delivery space 780 formed between the first and second shells 770, 775. The second shell 775 may have a plurality of apertures 785 for placing the delivery space 780 in communication with the pocket around the implant. Also, the delivery space 780 may be in fluid communication with a pocket port, such as pocket port 755.

The delivery canals described herein with respect to FIGS. 7A-B and other figures may have any cross-sectional shape, which may include rounded, circular, elliptical, elongated, triangular, rectangular, crescent, or any other shape.

Figure 8:
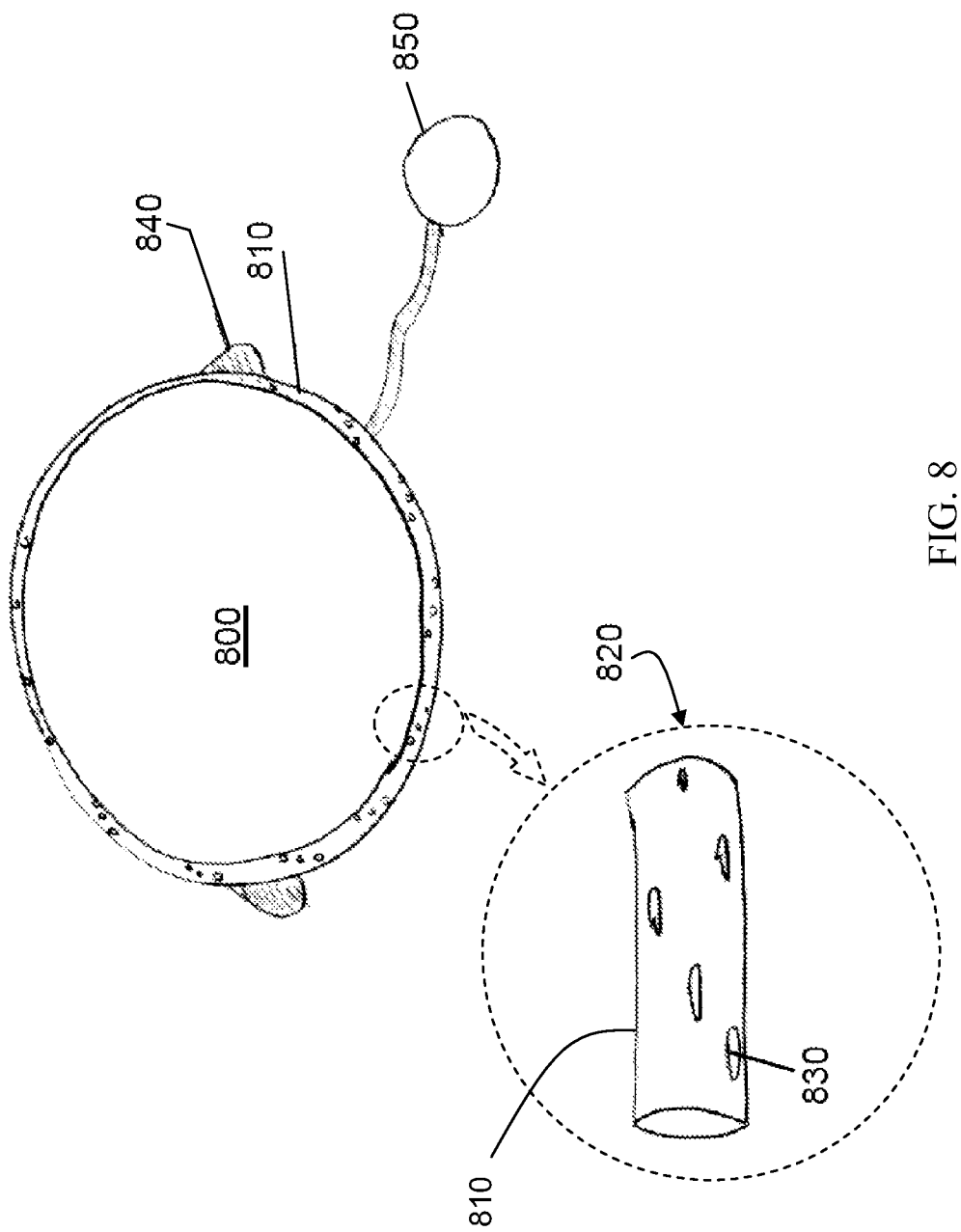
FIG. 8 shows a posterior view of a tissue expander with a delivery canal in accordance with aspects of the invention.

FIG. 8 shows a posterior view of a tissue expander 800 with a delivery canal 810. The delivery canal may be provided around the circumference of the tissue expander 800. In some embodiments, the delivery canal 810 may or may not also be provided along the posterior surface of the tissue expander 800 as one or more canals, sacs, regions, or layers. Furthermore, in some embodiments, the delivery canal 810 may encircle the entire circumference of the tissue expander 800, or may only go around a portion thereof. For example, the delivery canal 810 may surround three quarters of the circumference, half the circumference, a third of the circumference, a quarter of the circumference, a fifth of the circumference, a sixth of the circumference, or any other portion of the circumference of the tissue expander 800. In some instances, the delivery canal 810 may be provided continuously around the portion of the circumference, or may be provided in separate sections, which may or may not be in fluid communication with one another.

A close-up view 820 of a delivery canal 810 is provided. The delivery canal 810 may be integral to the posterior and outer edge of the implant shell. The delivery canal 810 may be formed of a soft material. However, the delivery canal may be formed of a material that is more non-compressible, sturdy or stiff than the implant shell defining the inside cavity of the tissue expander. The delivery canal 810 may include one or more small openings, holes, channels, or pores 830. These openings 830 may be arranged in any pattern. For example, they may be provided in a french drain type pattern on the delivery canal 810. The openings 830 may form a spiral pattern, or an array type pattern, or rows or columns, a staggered configuration, or any other suitable pattern or configuration.

In embodiments, one or more stability tabs 840 may be provided for a tissue expander in accordance with aspects of the invention. FIG. 8 shows an example of a tissue expander with two stability tabs 840. The two stability tabs 840 may be provided on opposing sides of the tissue expander. The stability tabs 840 may preferably be provided on a posterior side of the tissue expander and/or may be along a circumference of the tissue expander. The stability tabs 840 may be connected to an implant shell of the tissue expander or may be connected to a delivery canal surface.

Any number of stability tabs 840 may be provided in accordance with aspects of the invention. For example, one, two, three, four, five, six, seven, eight, nine, or ten or more stability tabs may be provided. The stability tabs may be evenly spaced around the circumference or of the tissue expander. Alternatively, the stability tabs need not be evenly spaced, and may have any arrangement on the tissue expander.

A stability tab 840 can be sewn to a portion of the patient's body. For example, one or more of the stability tabs may be sewn into a chest wall or any other support structure. In some instances, a stability tab can be a solid structure which may serve to prevent the implant from being turned over or accidentally flipping over during normal use. Thus, the tabs may or may not be sewn down.

Figure 9:
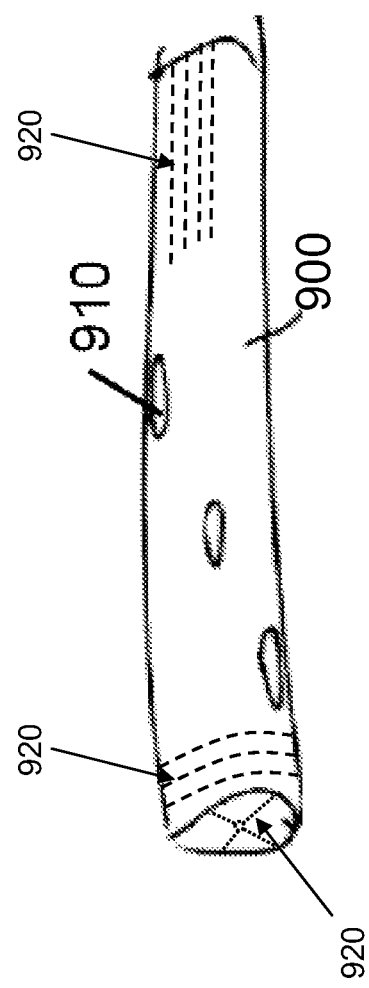
FIG. 9 shows an example of a delivery canal in accordance with aspects of the invention.

FIG. 9 provides another view of a delivery canal 900, which may be similar in structure and/or function to other delivery canals described with respect to other figures herein. The delivery canal 900 may have holes 910 or other openings, channels, pores, which may encircle the delivery canal, such as in a french drain configuration. The holes 910 of the delivery canal 900 may be provided so that access to fluid can be provided in different directions. Thus, fluid may be directed in an anterior, lateral or posterior direction.

As previously discussed, the delivery canal 900 may have any cross-sectional shape or size. In some instances, the delivery canal 900 may have a roughly circular cross-section, while in other examples, the delivery canal 900 may be substantially elliptical, triangular, rectangular, hexagonal, crescent-shaped, trapezoidal, or any other shape or configuration. The delivery canal 900 cross-sectional shape may remain substantially the same along its length, or may vary.

The delivery canal 900 may also have any cross-sectional size. For example, the height of the delivery canal 900 may be approximately half the height of the inside cavity defined by the implant shell, a third of the height of the inside cavity, a quarter of the height of the inside cavity, a fifth the height of the inside cavity, one sixth the height of the inside cavity, one eighth the height of the inside cavity, one tenth the height of the inside cavity, one-twentieth the height of the inside cavity, one fortieth the height of the inside cavity, one-hundredth the height of the inside cavity, or any other relative dimension. The delivery canal cross-sectional size may remain substantially the same along its length, or may vary. The holes 910 may have any desired shape that facilitates draining fluid from and delivering fluid to the pocket, e.g., pocket 630.

In embodiments, the delivery canal 900 (and other delivery canals and channels described herein) is more rigid than the implant shell (such as implant shell 615). This is because the implant shell is relatively pliable to permit inflation and deflation of the tissue expander device. The delivery canal, on the other hand, is relatively rigid to prevent its collapse and provide an unobstructed fluid pathway between the pocket and the pocket port.

According to aspects of the invention, using different materials to construct the implant shell and the delivery canal/channel, respectively, provides the different relative stiffness difference between the implant shell and delivery canal/channel. For example, the implant shell may be composed of a relatively pliable plastic (or other material), while the delivery canal/channel is composed of a more rigid plastic (or other material). Alternatively, the implant shell and delivery canal/channel may be formed of the same material or different materials, and the delivery canal/channel may be provided with a thicker wall than the wall of the implant shell, the relatively thicker wall providing the delivery canal/channel with more rigidity than the relatively thinner wall of the implant shell. Alternatively, the implant shell and delivery canal/channel may be formed of the same material or different materials, and the delivery canal/channel may be provided with reinforcing members 920. The reinforcing members 920 may be any suitable material and any suitable shape. For example, the reinforcing members 920 may comprise fiber, plastic, metal, or other materials arranged longitudinally, circumferentially, radially, randomly, or otherwise, on or in the wall of the canal 900 (or channel 610). The reinforcing members 920 impart a stiffness to the delivery canal/channel to make the delivery canal/channel more rigid than the implant shell.

Figures 10A, 10B:
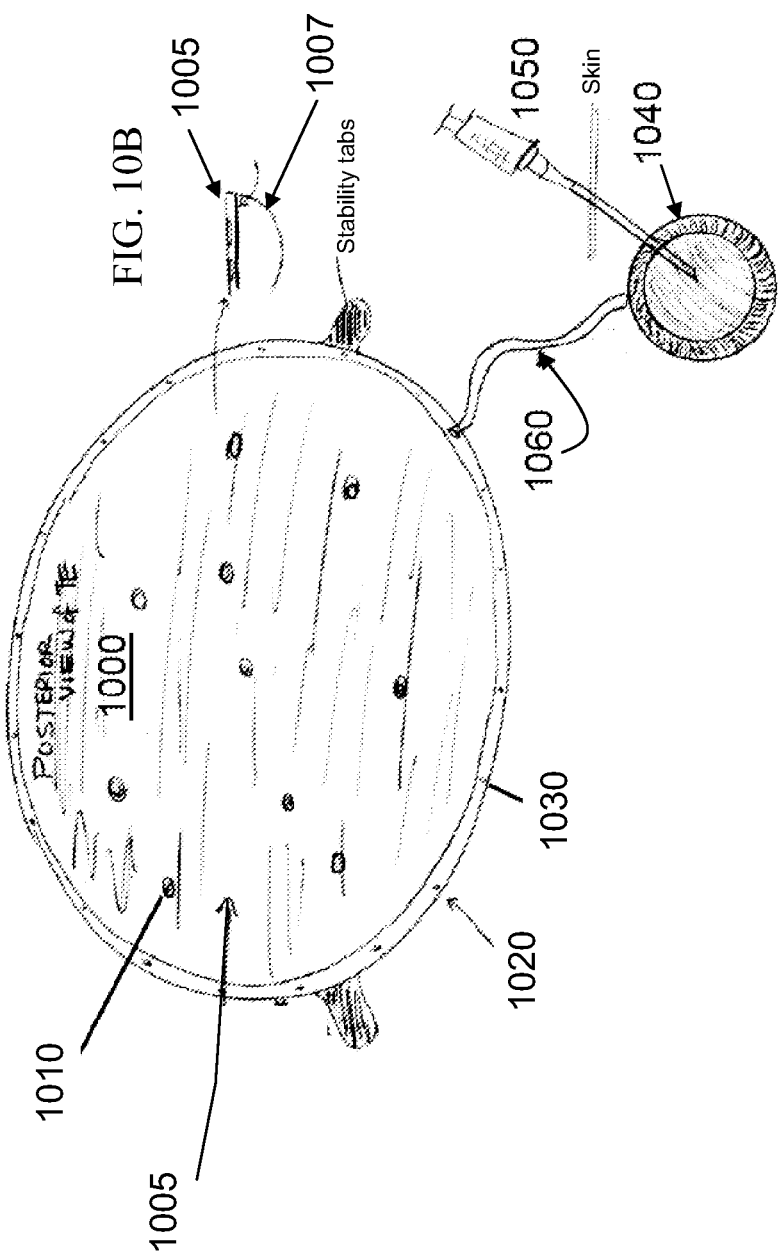
FIGS. 10A and 10B show an additional posterior view of a tissue expander with a delivery and/or retrieval region in accordance with aspects of the invention.

FIG. 10A shows an additional posterior view of a tissue expander with a fluid delivery and/or retrieval region 1000, e.g., similar to the double-wall embodiment described above with respect to FIG. 7B. That is, in embodiments, the delivery and/or retrieval region 1000 may comprise a second shell 1005 that covers a substantial portion of the implant shell 1007, creating a delivery space between the second shell 1005 and the implant shell 1007. Moreover, the second shell 1005 has openings 1010 that place the delivery space in fluid communication with the pocket in the patient's body. In some instances, the delivery and/or retrieval region 1000 may cover a posterior side of the tissue expander, as shown in FIG. 10B. In other embodiments, the delivery and/or retrieval region 1000 may cover an anterior or lateral side of the tissue expander. In some instances, the delivery and/or retrieval region 1000 may cover all sides of the tissue expander, e.g., the second shell 1005 may envelop substantially all of the implant shell 1007 to provide a double-wall configuration (similar to that associated with delivery canal 710e) around substantially the entire implant shell 1007.

In one example, the delivery and/or retrieval region 1000 may be a covering, e.g., second shell 1005, across the posterior/back of the tissue expander. The delivery and/or retrieval region 1000 may be used to either deliver fluid or retrieve fluid from the surrounding region. In one example, the covering can be like a plastic tarp that is secured to the tissue expander base. This covering, e.g., second shell 1005, may have holes 1010 it in like drainage pipes (e.g., french drain), which may allow fluid to be aspirated or delivered behind the implant. Thus, the covering, e.g., second shell 1005 may be a thin layer which allows transmission of fluid. The transmission of fluid may be to deliver a fluid to a pocket around the tissue expander, or to drain serous fluid that commonly develops where it may be difficult to stick a needle to remove. This may be advantageous in situations where the pocket surrounding the tissue expander is hypovascular in which there is a need to increase antibiotics delivery to the pocket. The implant may hold the space in the pocket.

A delivery canal 1020 may also be provided to the tissue expander. The delivery canal 1020 may have any configuration, as described elsewhere herein, such as with respect to delivery canals 900, 810, 710, and channel 610. In some embodiments, the delivery canal 1020 may or may not be in fluid communication with the delivery and/or retrieval region 1000. The delivery canal 1020 may or may not be an integral part of the delivery and/or retrieval region 1000.

The delivery canal 1020 may be formed of a relatively hard material that may resist collapse. In some embodiments, the delivery canal 1020 may be formed of a harder plastic material than the implant shell. The delivery canal 1020 may also be harder or stiffer than the covering 1005 used for the delivery and/or retrieval region 1000. The delivery canal 1020 may have holes 1030 that may allow fluid, medication, and/or aspiration to be delivered into the pocket. Alternatively, the delivery canal 1020 may withdraw fluid (e.g., seroma) from the pocket.

An implant utilizing a delivery canal 1020 and a delivery/retrieval region 1000 may allow tissue expansion while proactively protecting against infection and/or treating pocket infection. The implant may also allow withdrawal of seroma or other fluids. For example, fluid may be removed to send for culture. In some instances, a delivery canal 1020 may be used for one purpose while the delivery region 1000 may be used for another. For example, one (e.g., the delivery canal 1020 or the delivery region 1000) may be used to deliver a fluid, while the other (e.g., the delivery region 1000 or delivery canal 1020) may be used to withdraw a fluid. Alternatively, they may both be used for the same purpose. Any number of delivery canals and/or delivery regions may be provided, each of which may be used to deliver or withdraw a fluid. The delivery canal 1020 and the delivery region 1000 may be provided with and communicate with different respective pocket ports. By having separate pocket ports, the delivery canal 1020 and the delivery region 1000 may be used for different purposes, as described above. Alternatively, the delivery canal 1020 and the delivery region 1000 may both be fluidly connected to a single pocket port.

In some embodiments, a remote port 1040, e.g., pocket port, may be provided. In some instances, the remote pocket port 1040 may be implanted under the skin of a subject. The remote pocket port 1040 may be accessible via a needle 1050 from outside the skin. The remote pocket port 1040 may be in fluid communication with a delivery canal 1020 and/or delivery region via a communication channel 1060. The communication channel 1060 may be large and strong enough to aspirate some fluid if it is desirable to drain the pocket or send a culture.

In some embodiments, a communication channel 1060 may be provided between a remote pocket port and a delivery canal 1020 and/or delivery region 1000 of the tissue expander. In other embodiments, two or more communication channels 1060 may be provided. The remote pocket port 1040 may allow a user to provide and/or retrieve the same fluid from a plurality of different communication channels 1060, or may enable a user to provide and/or retrieve different fluids from the plurality of communication channels 1060. In other embodiments, the pocket port need not be remote, but may be provided integral to the tissue expander.

Figure 11:
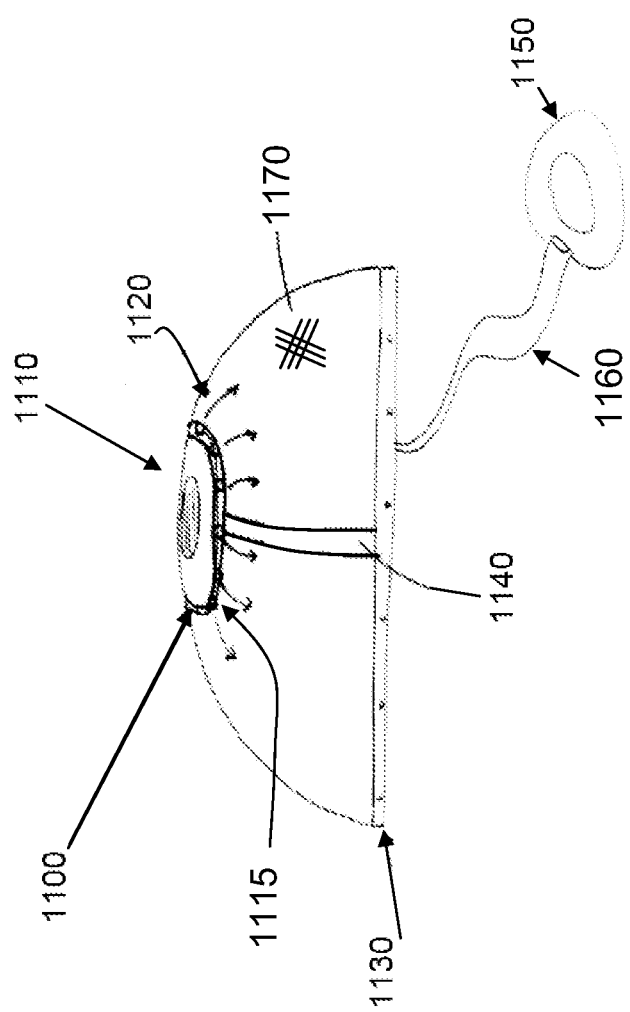
FIG. 11 shows an example of a tissue expander with an additional delivery canal in accordance with aspects of the invention.

FIG. 11 shows an example of a tissue expander with an additional delivery canal 1100. The additional delivery canal 1100 may be provided at any location on the tissue expander. In one example, the additional delivery canal 1100 may comprise a channel 1115 which may encircle at least a portion of an access port 1110 (which may be similar to access ports 410, 620, 720, etc.) usable for inflating and/or deflating the tissue expander. In some instances, the channel 1115 may be provided on the anterior side of the tissue expander, and thus may be an anterior channel. The channel 1115 may entirely encircle the access port 1110 or may encircle a portion of the access port 1110. The additional delivery canal 1100 may or may not have a circular shape. However, any description of the channel 1115 may also apply to channels of other shapes.

The channel 1115 may enable injection of fluid that may run down over exterior or interior surfaces the implant 1120. The channel 1115 may include one or more holes, channels, openings, or pores that may enable fluid to pass through, similar to holes 910 in delivery canal 900. Fluid may come out of the holes and run over the implant. The holes of the channel 1115 may have a french drain configuration, such as already described herein with respect to channel 610, delivery canal 900, etc., or any other configuration.

The tissue expander may also include a delivery canal 1130 near the posterior side of the tissue. The delivery canal 1130 may have any configuration as described herein, such as channel 610, delivery canal 710, delivery canal 810, delivery canal 910, etc. In embodiments, the channel 1115 may be located on the anterior side of the tissue expander and the delivery canal 1130 may be located on the posterior side of the tissue expander. In some embodiments, the delivery canal 1130 may be in fluid communication with the channel 1115 of the additional delivery canal 1100. For example, one or more communication channels 1140 may be provided between the delivery canal 1130 and the channel 1115. The one or more communication channels 1140 may have a flattened configuration, or any other suitable configuration that provides fluid communication between the delivery canal 1130 and the channel 1115.

Thus, fluid may be initially provided to the delivery canal 1130 or the channel 1115, respectively, and may flow to the other one of the delivery canal 1130 or the anterior channel 1115. For example, a remote pocket port 1150, which may be similar to any of the pocket ports described herein, may be provided in fluid communication with the delivery canal 1130. Fluid may be provided to the delivery canal 1130 via the remote pocket port 1150, and then may flow through one or more communication channels 1140 to the channel 1115. Fluid may extrude from the delivery canal 1130 and/or channel 1115. In another example, the remote pocket port 1150 may be in fluid communication with the channel 1115. Thus, fluid may be provided to the channel 1115 via the remote pocket port 1150, and then may flow through a communication channel to the delivery canal 1130. A remote pocket port 1150 may be used for ease of access in placement of fluids.

In embodiments, a communication channel 1160 may fluidly connect the remote pocket port 1150 and the delivery canal 1130 to provide fluid communication between the remote pocket port 1150 and the delivery canal 1130. Also, communication channel 1140 may fluidly connect the delivery canal 1130 and the additional delivery canal 1100 to provide fluid communication between the delivery canal 1130 and the additional delivery canal 1100. In this manner, fluid that is injected into the single remote pocket port 1150 may flow out of the holes of the delivery canal 1130 and also flow out of holes of the additional delivery canal 1100 into the pocket in the patient's body. Similarly, fluid may be extracted from the pocket via both the delivery canal 1130 and the additional delivery canal 1100 via the single remote pocket port 1150.

In another example, the pocket port 1150 need not be remote from the tissue expander, but rather may be provided integral to the implant shell of the tissue expander. For example, the pocket port 1150 may be built into or on the implant shell next to the implant port 1110. Such an integral pocket port may provide fluid first to a delivery canal 1130 or to the channel 1115. With either configuration, fluid may extrude from the delivery canal 1130 and/or channel 1115.

In other embodiments, separate pocket ports may be provided for the delivery canal 1130 and the channel 1115, respectively. In some instances, the separate pocket ports need not be in fluid communication with one another and, similarly, the delivery canal 1130 and the channel 1115 need not be in fluid communication with each other. In other examples, a single pocket port may be provided that may provide different fluids to the delivery canal 1130 and the channel 1115. Any number of additional channels or regions may be provided, which may or may not be in fluid communication with the delivery canal 1130 and/or channel 1115. Any of the channels or regions described herein may also be used for drainage purposes, so that fluid may be removed from the surrounding pocket, rather than delivered to the pocket.

Still referring to FIG. 11, in embodiments the tissue expander may have a covering 1170. The covering 1170 may include a coating. The coating may be an antibiotic coated material which may leach out. The coating may also have a heavy metal which may be anti-microbial resistant.

Any fluid may be provided to the pocket around the tissue expander via the delivery systems described herein. Such fluids may be liquids, air or any other gas. In some instances, the fluids delivered may include antibiotics, anti-microbial solutions, heavy metals, anesthetics, extracellular matrix digestive enzymes, growth factors (e.g., epidermal growth factor (EGF), fibroblast growth factor (FGF), platelet-derived growth factor (PDGF), angiogenic growth factor), or agents that inhibit fibrosis, capsule formation and/or scar formation.

Any fluid may be retrieved from the pocket around the implant via the delivery/retrieval system. Such fluids may include liquids or gases, or combinations thereof. In one example, seroma maybe removed from the pocket. It may be desirable to drain any sort of fluid from the pocket in order to perform a culture or diagnostics on the fluid.

Port Configurations

As previously discussed, in accordance with aspects of the invention, one or more ports may be provided to a tissue expander. In some embodiments, an access port (also called an implant port herein) may be provided to enable a fluid to be delivered to an inside cavity for inflation and deflation of the tissue expander. In some embodiments, the same port, or a separate delivery port (also called a pocket port herein) may be used to deliver or retrieve a fluid from a delivery canal (which may encompass a delivery region or system). The delivery port may be a remote port that is remote from the implant shell of the tissue expander or may be an integrated port that is integral with or otherwise arranged on or in the implant shell of the tissues expander.

Figure 12B:
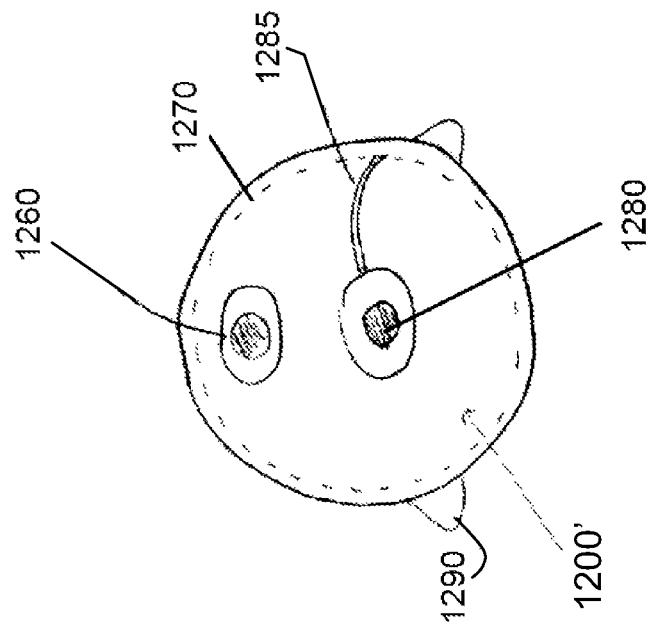
FIG. 12B shows an example of a tissue expander with an integrated port in accordance with aspects of the invention.
Figure 12A:
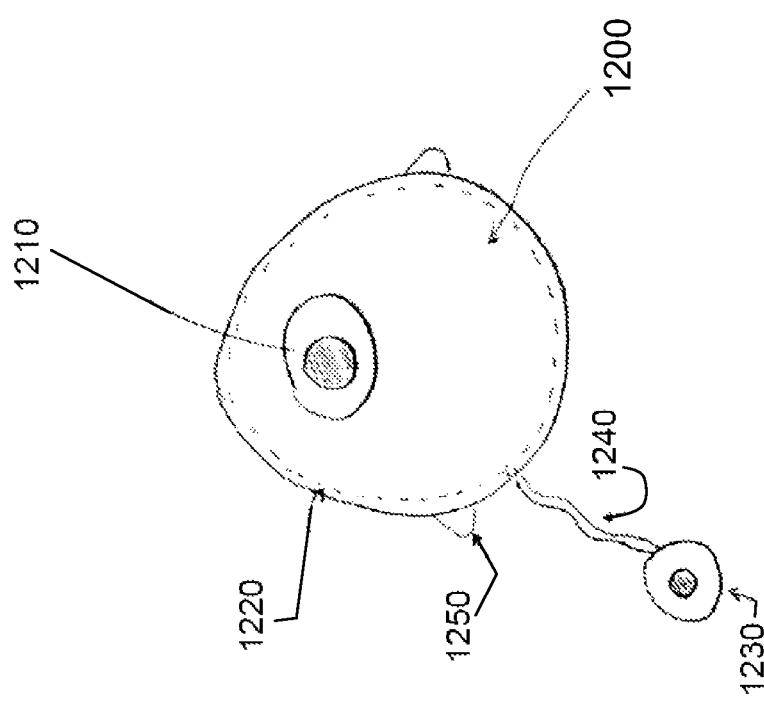
FIG. 12A shows an example of a tissue expander with a remote port in accordance with aspects of the invention.

FIG. 12A shows an anterior view (e.g., top down as if the patient were laying flat on the table) of a tissue expander 1200 with a remote pocket port 1230. The tissue expander 1200 may include an inflatable and deflatable implant shell, as described herein. The tissue expander 1200 may be formed of any composition. In some embodiments, the tissue expander 1200 may include an external antibacterial or antimicrobial coating on at least a portion of the exterior surface of the implant shell. The tissue expander may include a access port 1210 integrated with the implant shell, the access port being similar to other access ports described herein and operable for inflating and deflating one or more cavities defined within the implant shell. In other embodiments, the access port 1210 may be remote from the implant shell and placed in fluid communication with one or more cavities defined by the implant shell via one or more communication channels, which may be tubes. The access port 1210 is not limited to these configurations and may have differing configurations. The access port 1210 may be located at the substantial center of the tissue expander 1200 when viewed from an anterior view. Alternatively, the access port 1200 may be offset to a side of the tissue expander 1200, or may be located at any other desired location.

The tissue expander 1200 may have a delivery canal 1220 which may encircle at least a portion of the circumference of the tissue expander 1200, or have any other configuration. The delivery canal 1220 may communicate with the remote pocket port 1230 via a communication channel 1240. The delivery canal 1220, pocket port 1230, and communication channel may be similar in structure and/or functionality to other delivery canals, remote pocket ports, and communication channels described herein with respect to other figures. In embodiments, one or more stability tabs 1250 may also be provided to the tissue expander 1200 for securing the tissue expander within the patient. The remote pocket port 1230 may enable fluids to be delivered via the communication channel 1240 to the delivery canal 1220, which may include openings or have a surface that may enable the fluid to reach a pocket surrounding the tissue expander.

FIG. 12B shows an anterior view of a tissue expander 1200' with an integrated access port 1260 and an integrated pocket port 1280. The tissue expander 1200' may include an implant shell as described herein. The tissue expander 1200' may be formed of any composition. In some embodiments, the tissue expander 1200' may include an external antibacterial or anti-microbial coating on at least a portion of the implant shell. The tissue expander 1200' may include an integrated access port 1260 that is formed integral with or otherwise on or in the implant shell. In other embodiments, the access port 1260 may be remote from the implant shell, or have differing configurations. The access port 1260 may be located at the substantial center of the tissue expander 1200' when viewed from an anterior view. Alternatively, the access port 1260 may be offset to a side.

The tissue expander 1200' may have a delivery canal 1270 which may encircle at least a portion of the circumference of the tissue expander 1200', or have any other configuration. The delivery canal 1270 may communicate with the integrated pocket port 1280 via a communication channel 1285. The integrated pocket port 1280 may be located at the substantial center of the tissue expander 1200' when viewed from an anterior view. Alternatively, the integrated pocket port 1280 may be offset to a side of the tissue expander 1200'. The communication channel 1285 may be between the integrated pocket port 1280 and the delivery canal 1270. In some embodiments, the communication channel 1285 may run along the exterior surface of the implant shell tissue expander or on the exterior of the tissue expander without running along the surface. Alternatively, the communication channel 1285 may run along the interior surface of the implant shell of the tissue expander or through the interior of the tissue expander without running along the surface.

One or more stability tabs 1290 may also be provided to the tissue expander. The integrated pocket port 1280 may enable fluids to be delivered via the communication channel 1285 to the delivery canal 1270, which may include openings or have a surface that may enable the fluid to reach a pocket surrounding the tissue expander. The delivery canal 1270, integrated pocket port 1280, and communication channel 1285 may be similar in structure and/or functionality to other delivery canals, integrated pocket ports, and communication channels described herein with respect to other figures.

Figure 13A:
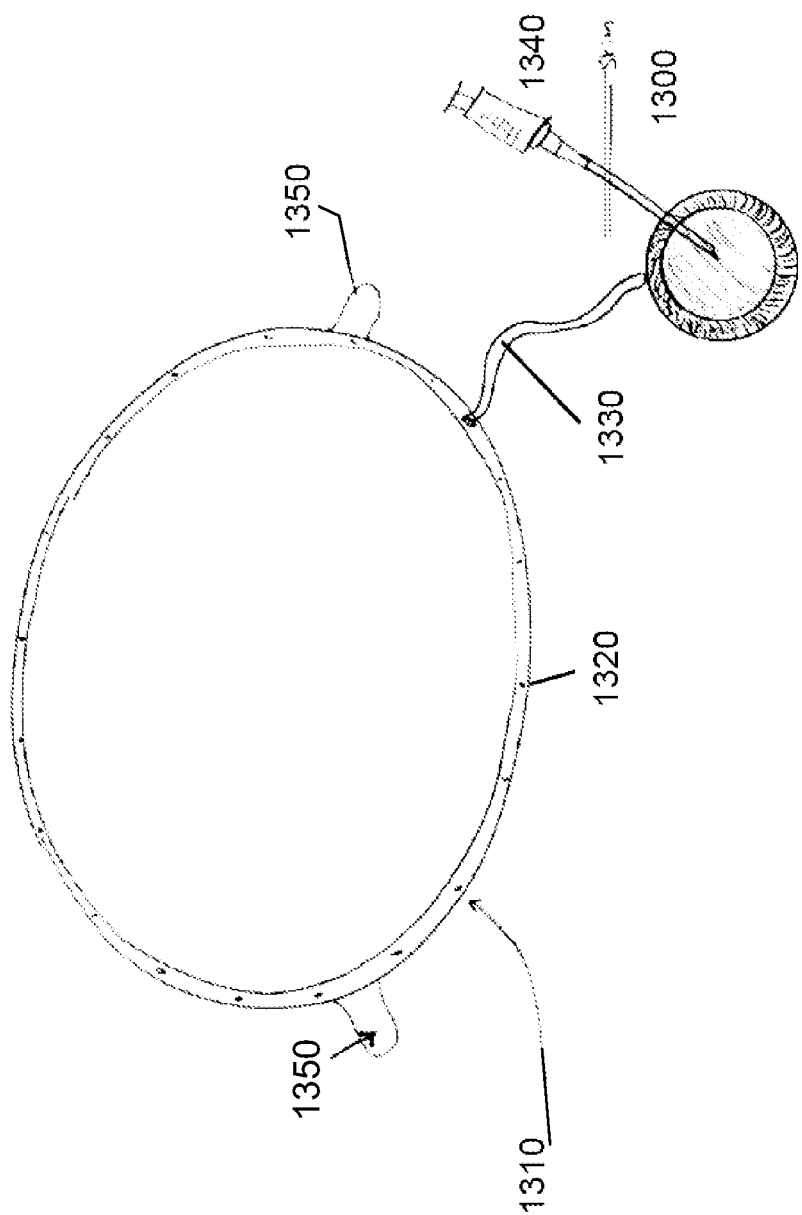
FIG. 13A provides another view of a tissue expander with a remote port in accordance with aspects of the invention.

FIG. 13A provides a posterior view of a tissue expander with a remote pocket port 1300, which provides a view of the portion of the tissue expander that may be adjacent to or facing toward a chest wall, or other support surface. A delivery canal 1310 may be provided with one or more holes 1320. The holes may be provided along the delivery canal 1310, which may allow fluid, such as medication, to be delivered into a pocket surrounding the tissue expander.

A remote pocket port 1300 may be connected to the delivery canal 1310 via a communication channel 1330. The delivery canal 1310, pocket port 1300, and communication channel 1330 may be similar in structure and/or functionality to other delivery canals, remote pocket ports, and communication channels described herein with respect to other figures. An anterior view of the remote pocket port 1300 is shown. The remote pocket port 1300 may be provided beneath the skin of a subject (e.g., patient). The remote pocket port 1300 may be accessible with a needle from outside of the skin. In some embodiments, the remote pocket port 1300 may include a magnetic or metallic component, so that a user may be able to use a magnet from outside the skin to detect the location of the remote pocket port 1300. For example, placing a magnet to the exterior of the skin may cause the remote pocket port 1300 to move in response to the magnetic force associated with the magnet. In alternate embodiments, the remote pocket port 1300 may be located external to the skin of the subject, or may include a component that extends outside the skin of the subject. The remote pocket port 1300 may or may not be removable from the subject and/or disconnected from the tissue expander.

A needle and syringe 1340 may be used to deliver fluid to the remote pocket port 1300. The syringe 1340 may provide a positive pressure that may cause a pressure differential that may enable fluid to be forced into the delivery canal 1310. In other embodiments, other delivery devices may be used to provide fluid to the remote pocket port 1300. Such delivery devices may include a positive pressure source, or any other configuration that may create a pressure differential. In some instances, it may be desirable to retrieve a fluid from a pocket surrounding the tissue expander. In such situations, a needle and syringe 1340 may be used to create a negative pressure and withdraw fluid from the pocket around the tissue expander through a combination of the delivery canal 1310, the communication channel 1330, and the remote pocket port 1300. Any other delivery system may be used which may provide a negative pressure external to the remote port or cause a desired pressure differential to retrieve fluid.

As previously described, one, two, or more tabs 1350, e.g., stability tabs, may be provided for securing the tissue expander within the patient's body. In some embodiments, the tabs 1350 may be used to sew the tissue expander to a chest wall or other supporting structure. The tabs 1350 may also be a solid piece or relatively rigid material that may stick out from the implant shell like a training wheel, or that may inhibit a flip over of the tissue expander.

Comparing FIG. 13A to FIG. 8, it can be seen that FIG. 8 depicts an additional view of a tissue expander with a remote pocket port 850 in which the posterior view of the remote pocket port 850 is provided. In some embodiments, the posterior and the anterior side of the remote pocket port may be different. For example, in some instances, only an anterior side of the remote pocket port may include a material that may enable a needle to penetrate to deliver a fluid. The material may be a self-healing (e.g., self-sealing) material. In some instances, the posterior side of the remote pocket port may include a sturdy material that may prevent the needle from extending through the posterior side of the pocket port. Thus, the needle end may be within the pocket port.

In another embodiment, the anterior and posterior side of the remote pocket port may be substantially the same. In some instances, a remote pocket port may be accessed by a needle from any side. Thus, if the remote pocket port were to rotate or flip, it may still be accessed. In such situations, it may be desirable for the pocket port to include a sturdy material inside which may prevent the needle from penetrating through the other side of the pocket port.

Figure 13B:
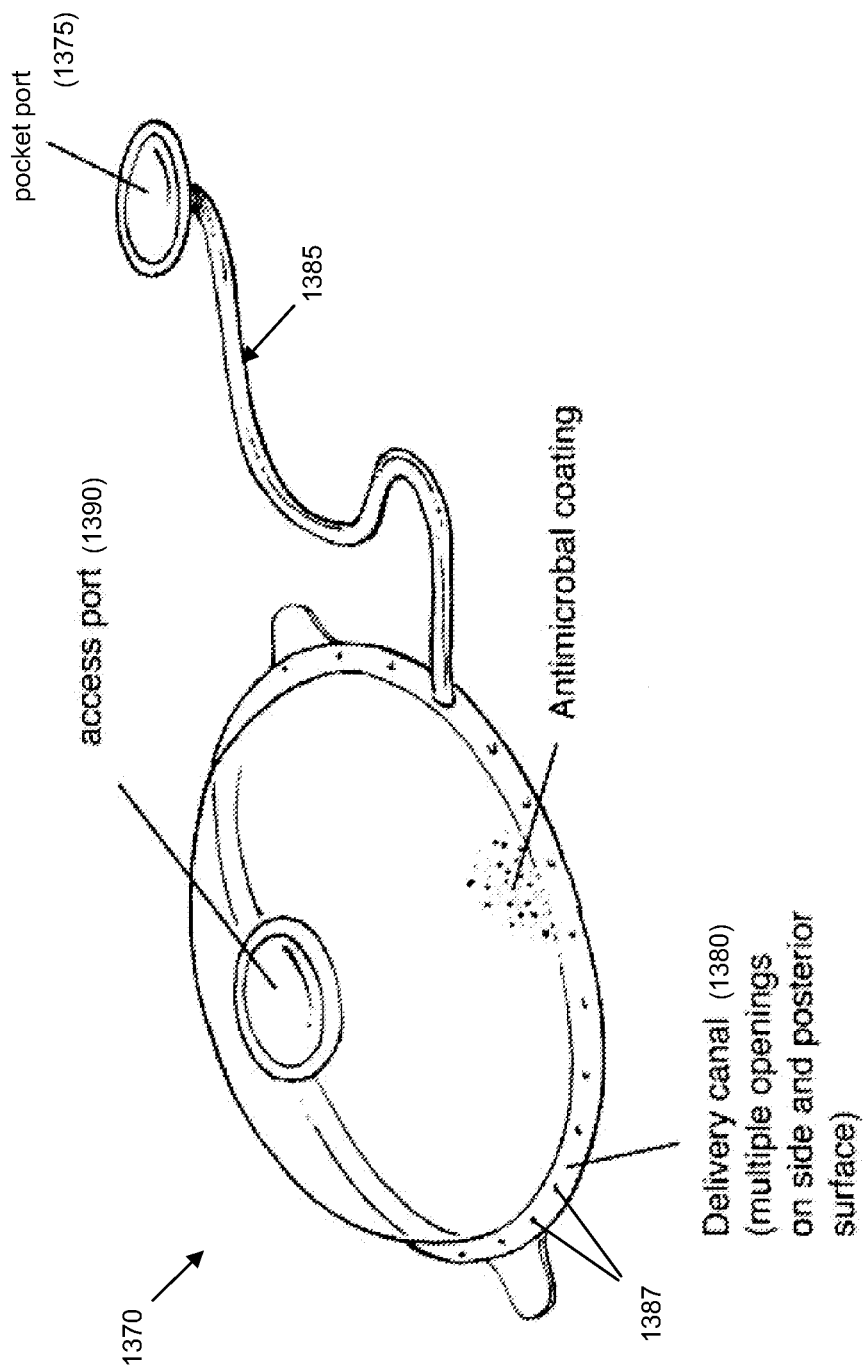
FIG. 13B provides an illustration of a tissue expander with a remote port in accordance with aspects of the invention.

FIG. 13B shows an additional view of a tissue expander 1370 with a remote pocket port 1375. The remote pocket port 1375 may be fluidically connected to a delivery canal 1380 via a communication channel 1385. The delivery canal 1380 may have one or multiple openings 1387 on the side and/or posterior surface of the tissue expander 1370 that place the interior of the delivery canal 1380 in fluid communication with a pocket surrounding the tissue expander 1370. An access port 1390 may be provided on the tissue expander 1370, which may provide fluidic access to the interior cavity of an implant shell of the tissue expander 1370 for inflating and deflating the tissue expander 1370.

Any one or more of the exterior surfaces of the components of the tissue expander 1370 may be covered with an antibiotic and/or antimicrobial coating. In some embodiments, a dissolvable cover, such as PDS or monocryl may be provided on any exterior surface of any component (e.g., implant shell, remote pocket port 1375, delivery canal 1380, communication channel 1385, access port 1390, etc.). Such a coating or cover may prevent the establishment of a biofilm, which may be a strong covering of the implant with bacteria. A dissolvable cover or coating may preferably dissolve away, preventing bacteria from attaching to the expander itself. A dissolvable cover may be used in conjunction with antibiotics and/or antimicrobial coatings, or may be used alone without requiring antibiotics or antimicrobial coatings.

Figure 14A:
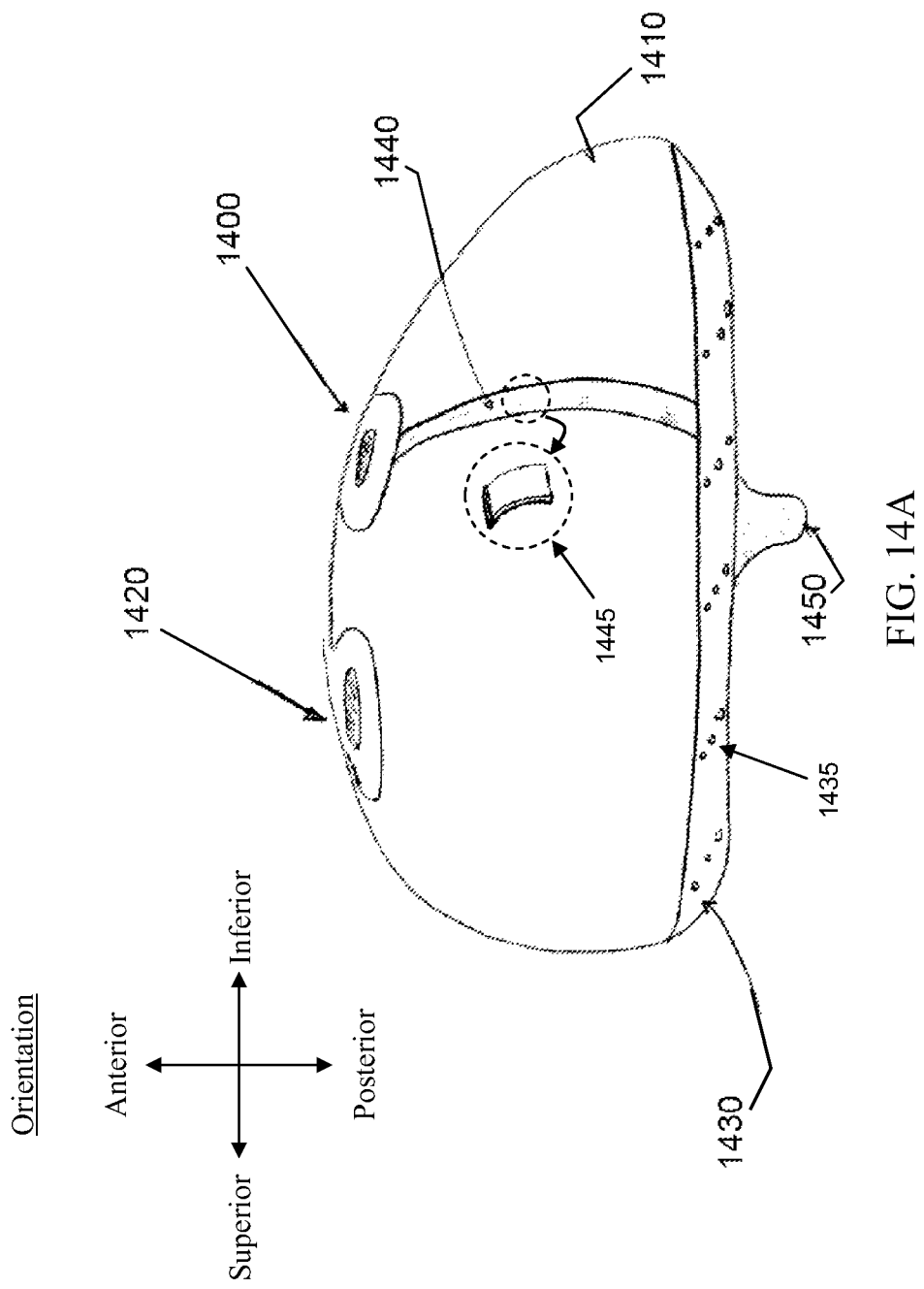
FIG. 14A shows a tissue expander with an integrated port in accordance with aspects of the invention.

FIG. 14A provides a side view of a tissue expander with an integrated pocket port 1400. The tissue expander may include an implant shell 1410 forming an internal cavity that may be inflated and deflated as described herein with respect to other implant shells. The implant shell 1410 may be formed of any composition known or later developed in the art. In some instances, the implant shell 1410 may have a coating, such as an external antimicrobial coating. The implant shell 1410 may also include an access port 1420 or any other access port known or later developed in the art that provides selective fluid communication with the interior of the implant shell for inflating and deflating the tissue expander. The access port 1420 may be an integrated access port 1420 in that the access port 1420 may be formed integral with or otherwise formed in or connected to the implant shell 1410. The access port 1420 may enable a practitioner to put saline (or other fluid) into the tissue expander as desired. Alternatively, the access port 1420 may enable a practitioner to remove a fluid from the tissue expander.

In accordance with aspects of the invention, an integrated pocket port 1400 may be provided as a separate port from the access port 1420. The integrated pocket port 1400 may be in fluidic communication with a delivery canal 1430 via a communication channel 1440. The delivery canal 1430 may comprise a plurality of openings 1435. The delivery canal 1430, integrated pocket port 1400, and communication channel 1440 may be similar in structure and/or functionality to other delivery canals, integrated pocket ports, and communication channels described herein with respect to other figures. The communication channel 1440 may be provided between the integrated pocket port 1400 and the delivery canal 1430 and may be built into or on the implant shell 1410. The communication channel 1440 may be relatively flat, e.g., have a width dimension substantially parallel to the surface of the implant shell 1410 that is much greater than a height dimension substantially perpendicular to the surface of the implant shell 1410, as depicted in the magnified cross section portion 1445. Alternatively, when it is desired to keep the exterior of the implant shell 1410 smooth, the communication channel 1440 may be internal to the implant shell 1410. Alternatively, the communication channel 1440 may protrude on the external and/or internal surface of the implant shell 1410.

In some embodiments, the integrated pocket port 1400 may protrude outward from an exterior surface of the implant shell 1410. Alternatively, the integrated pocket port 1400 may be internal to the implant shell 1410, so that it does not protrude outward from an exterior surface of the implant shell 1410. The integrated pocket port 1400 may be provided on an anterior side of the tissue expander. The integrated pocket port 1400 may include a penetrating surface that may enable a needle to penetrate to deliver a fluid. The material of the penetrating surface may be a self-healing material in that a hole in the material created by a needle is automatically sealed to a fluid-tight state after removal of the needle from the material. In some embodiments, the integrated pocket port 1400 may include a sturdy material on the other side of the penetrating surface to prevent the needle from penetrating too far into and/or through the integrated pocket port 1400. This may be desirable, for example, to prevent the needle from penetrating into the inside cavity of the implant shell 1410 of the tissue expander.

FIG. 14A also shows a side view of the tissue expander with a stability tab 1450. The stability tab 1450 may lie flat against a firm area such as a chest wall or other bodily support structure. Alternatively, the stability tab 1450 may angle downwards or upwards with respect to the implant shell 1410, as desired.

Figure 14B:
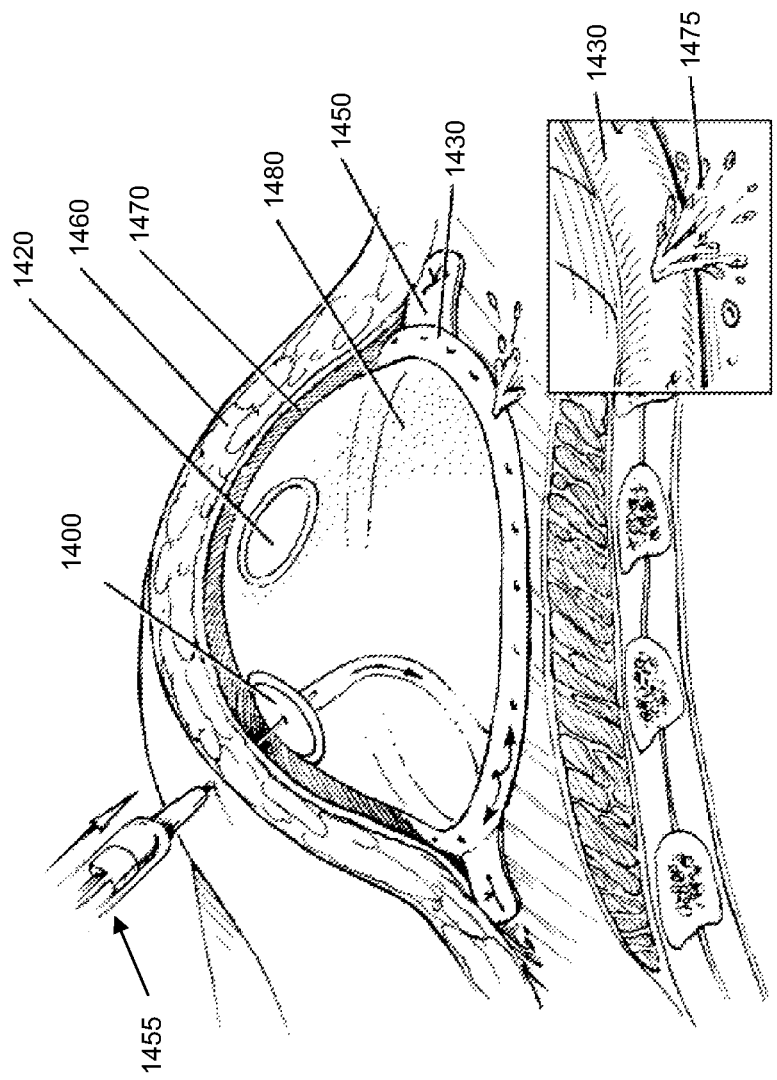
FIG. 14B shows an additional view of a tissue expander with an integrated port in accordance with aspects of the invention.

FIG. 14B shows an additional view of the tissue expander of FIG. 14A implanted in a patient. In embodiments, the tissue expander is provided with an integrated pocket port 1400 and an integrated access port 1420. The pocket port 1400 may be fluidically connected to a channel system comprising the delivery canal 1430 having multiple openings. Fluid may be provided via needle 1455 through the pocket port 1400 to the delivery canal 1430 and out to the area surrounding the tissue expander, e.g., the pocket. In some embodiments, the fluid may be an antibiotic solution.

The tissue expander may be provided under the skin and/or subcutaneous tissue 1460 of a subject. A pocket 1470 may be provided as the potential space between the tissue expander and the capsule, or tissue surrounding the tissue expander. When fluid 1475 is delivered through the delivery canal 1430, it may be delivered to the pocket surrounding the tissue expander.

One or more stability tabs 1450 may be provided on the tissue expander. In some embodiments, the stability tabs 1450 may protrude from beneath the delivery canal 1430.

The tissue expander may have an antibiotic and/or antimicrobial coating 1480. In some embodiments, the tissue expander may have a dissolvable cover such as PDS or Monocryl. The dissolvable cover, which may or may not be used in combination with an antibiotic or antimicrobial coating, may prevent or delay the establishment of a biofilm. As the dissolvable cover dissolves away, bacteria loses the ability to attach to the tissue expander, thereby inhibiting the growth of the biofilm.

Figure 15A:
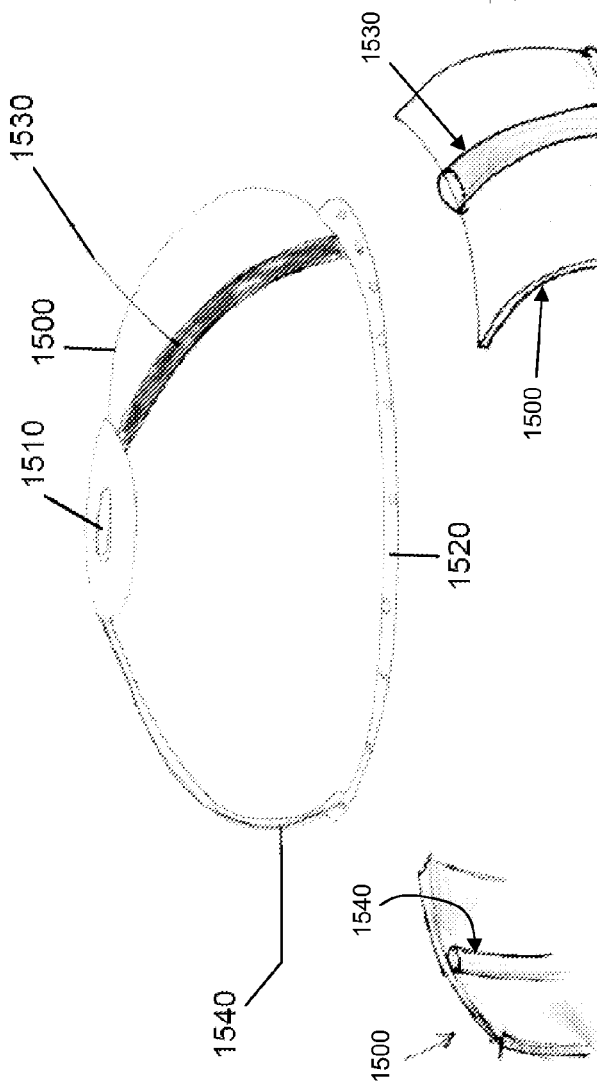
FIGS. 15A-D show a tissue expander with an integrated port with communication channels in accordance with aspects of the invention.

FIG. 15A shows a tissue expander comprising an implant shell 1500, an integrated pocket port 1510, a delivery canal 1520 with a plurality of openings, a first communication channel 1530, a second communication channel 1540. The delivery canal 1520, integrated pocket port 1510, and communication channels 1530 and 1540 may be similar in structure and/or functionality to other delivery canals, integrated pocket ports, and communication channels described herein with respect to other figures.

The tissue expander may have an inside cavity formed by the implant shell 1500. The first communication channel 1530 may be provided between the integrated pocket port 1510 and the delivery canal 1520 to provide fluid communication between the integrated pocket port 1510 and the delivery canal 1520. The first communication channel 1530 may be provided on an external surface of the tissue expander, or can be within the tissue expander so the outside surface remains smooth. As shown in FIG. 15B, the first communication channel 1530 may be external to the implant shell 1500. This may cause the first communication channel 1530 to protrude from an exterior surface of the implant shell 1500.

Figure 15C:
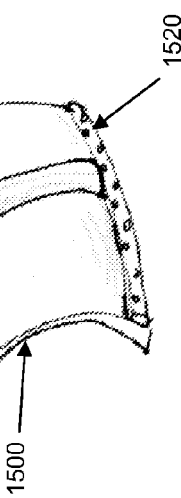
Figure 15B:
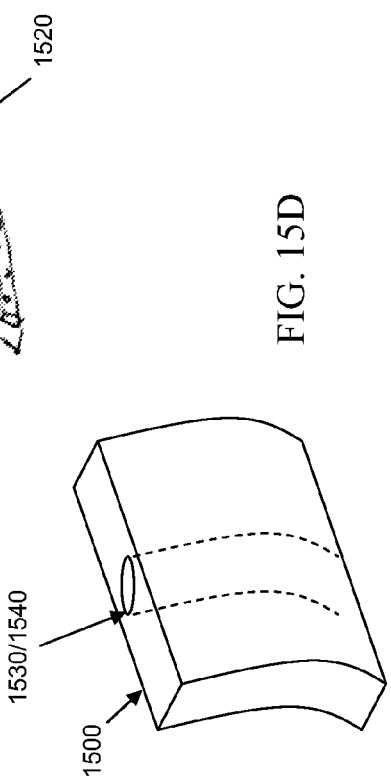

In embodiments, and as shown in FIG. 15C, the second communication channel 1540 may be provided within the interior of the implant shell 1500 of the tissue expander and also provide fluid communication between the integrated pocket port 1510 and the delivery canal 1520. The second communication channel 1540 may be integral to the implant shell 1500 wall or adhered to it. The second communication channel 1540 may be adhered to the wall using a glue or any other adhesive. In some instances, when the second communication channel 1540 reaches the posterior portion of the tissue expander, it may transition through the implant shell 1500 to the external delivery canal 1520. Alternatively, the delivery canal 1520 may be interior to the tissue expander, in which case such transition may not be necessary.

Figure 15D:

In embodiments, at least one of the first communication channel 1530 and the second communication channel 1540 may be integral to the implant shell 1500 so that the communication channels 1530, 1540 may protrude on both the external and internal sides of the implant shell 1500. In another example, the implant shell 1500 thickness may be sufficient so that the first communication channel 1530 protrudes from neither the external nor internal sides of the implant shell 1500. For example, as depicted in FIG. 15D, at least one of the first communication channel 1530 and the second communication channel 1540 may be contained within a thickness of a wall of the implant shell 1500 such that the at least one of the first communication channel 1530 and the second communication channel 1540 constitute a duct formed within the wall of the implant shell. In other embodiments, at least one of the first communication channel 1530 and the second communication channel 1540 may run through the interior cavity of the tissue expander without being directly connected to the implant shell 1500, or may run external to the tissue expander without being directly connected to and/or integral to the implant shell 1500.

The first communication channel 1530 and the second communication channel 1540 may achieve the same functionality, whether internal or external to the implant shell. In particular, the first communication channel 1530 and the second communication channel 1540 may provide fluid communication between a pocket port 1510 (which may be accessible externally from the patient) and the pocket surrounding the tissue expander implant. In embodiments, at least one of the first communication channel 1530 and the second communication channel 1540 may branch off from a lumen within the pocket port 1510. In embodiments, at least one of the first communication channel 1530 and the second communication channel 1540 may intersect (and be fluidically connected to) one or more delivery canals 1520.

Any number of communication channels, such as communication channels 1530 and 1540, may be provided to provide fluid communication between the pocket port and the delivery canal. In some embodiments, one communication channel is provided between a pocket port and a delivery canal. In other embodiments, a plurality of communication channels, such as two, three, four, five, six, eight, ten, fifteen, twenty, or more communication channels may be provided. The communication channels may branch off from the same pocket port or multiple separate pocket ports. The communication channels may be provided so that they are evenly spaced around the tissue expander, or may have any other spatial configuration with relation to the tissue expander surface. The same configuration or different configuration of communication channels may be utilized for a tissue expander.

In embodiments, one or more communication channels may be provided between a single pocket port and a single delivery canal. In other embodiments, one or more communication channels may be provided between a plurality of pocket ports and a single delivery canal, a single pocket port and a plurality of delivery canals, or a plurality of pocket ports and a plurality of delivery canals. The same type of fluid or different types of fluids may be delivered and/or retrieved through the communication channels.

Figure 16A:
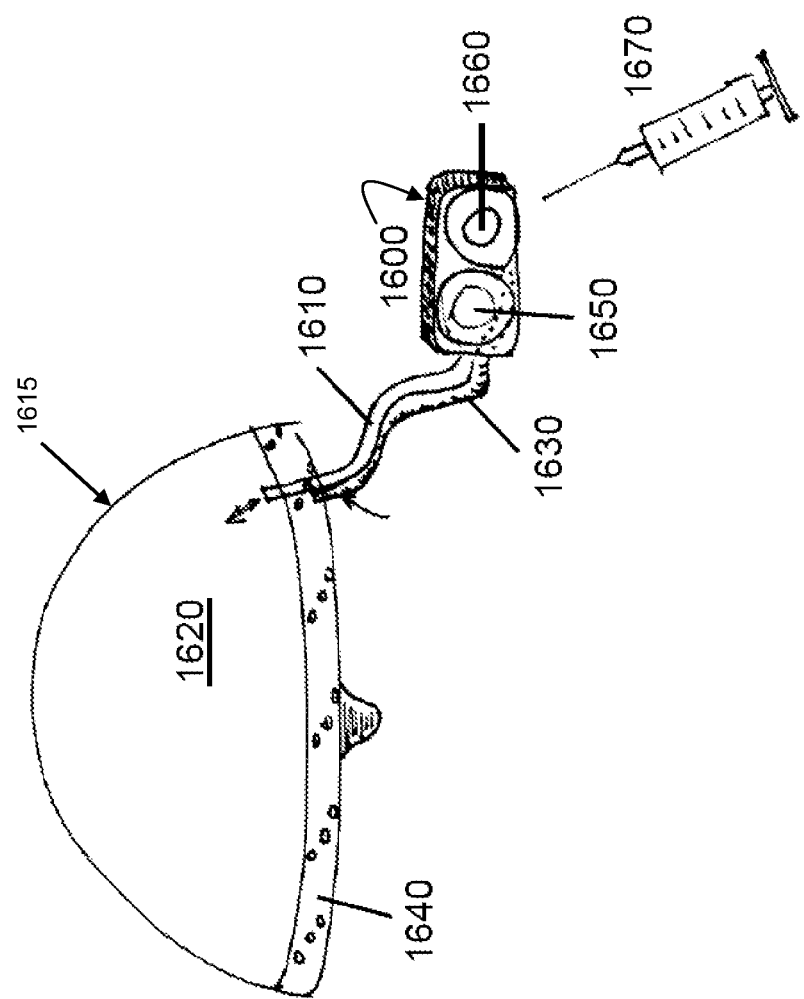
FIG. 16A illustrates an example of a dual remote port in accordance with aspects of the invention.

FIG. 16A illustrates an example of a dual remote port 1600. The dual remote port 1600 may be connected to a first communication channel 1610 that may communicate with the interior of an implant shell 1615 of a tissue expander 1620 for inflation/deflation of the tissue expander. The dual remote port 1600 may also be connected to a second communication channel 1630 that may communicate with a channel system comprising a delivery canal 1640 for delivery/extraction of fluid to/from the pocket around the tissue expander. Preferably, the interior of the tissue expander and the channel system are not in fluid communication with one another.

The dual remote port 1600 may include two ports, such as an implant port 1650 (also called an access port) and a pocket port 1660. The implant port 1650 may be in fluidic communication with the first communication channel 1610 and the interior of the implant shell 1615 of the tissue expander 1620. The pocket port 1660 may be in fluidic communication with the second communication channel 1630 and the channel system comprising the delivery canal 1640. In embodiments, the implant port and the pocket port are fluidically isolated from one another.

In embodiments, the dual remote port 1600 comprises a housing or other structure that is directly connected to both the implant port 1650 and the pocket port 1600. The first communication channel 1610 and the second communication channel 1630 are of sufficient length such that the dual remote port 1600 may be located a substantial distance away from the implant shell 1615 of the tissue expander 1620. In this manner, the dual remote port 1600 provides the ability to inflate and deflate the implant shell via the implant port 1650, and also the ability to inject/extract fluid to/from the pocket via the pocket port 1660, at a single location that is remote from the implant shell 1615 of the tissue expander 1620.

The dual remote port 1600 may be configured to receive fluid from a needle and syringe 1670. Any other fluid delivery system may be used. Preferably, a first fluid is delivered through the implant port 1650, and a second fluid is delivered through the pocket port 1660. In some instances, the first fluid may include saline, buffered saline, water, air, or any other fluid that may be provided to the inside cavity of an implant. The second fluid may include medication, antibiotics, antimicrobial solutions, or any other fluid to deliver to the pocket surrounding the tissue expander. In other embodiments, the implant port 1650 and/or pocket port 1660 may be used to retrieve a fluid from the inside of the implant or the pocket surrounding the implant, respectively.

The dual remote port 1600 may be implanted under the skin of a subject. The ports 1650 and 1660 in the dual remote port may be provided with a magnet. This may enable the ports 1650, 1660 to be found beneath the skin. A plurality of ports, such as the implant port 1650 and the pocket port 1660, may be differentiated beneath the skin. In embodiments, this differentiation may be provided by having reverse polarity on the magnets in the ports. For example, a first finding magnet may be attracted to the implant port 1650 and second finding magnet of different polarity than the first finding magnet may be attracted to the pocket port 1660. For example, positive side of a magnet may attract an implant port 1650 while a negative side of the magnet may attract the pocket port 1660, or vice versa. This way, a practitioner can distinguish between the two ports 1650, 1660 and determine which fluid needs to be injected into or retrieved from each port.

Although two ports 1650, 1660 are provided by way of example, any number of ports may be utilized in a dual remote access port. The various ports may be distinguished by spatial placement in addition to magnetic polarity. For example, it may be predetermined that certain ports may be accessed close to a certain region of the subject's body. For example, some types of ports (e.g., implant ports) may be placed on a first side (e.g., to the right side) of an implant while different types of ports (e.g., pocket ports) may be placed on a second side opposite the first side (e.g., to the left side) of the implant. This may enable detection and identification of additional subcutaneous ports. This may be desirable in situations where more than two fluids may be delivered and/or retrieved from a subject's tissue expander or region surrounding the tissue expander.

Figure 16B:
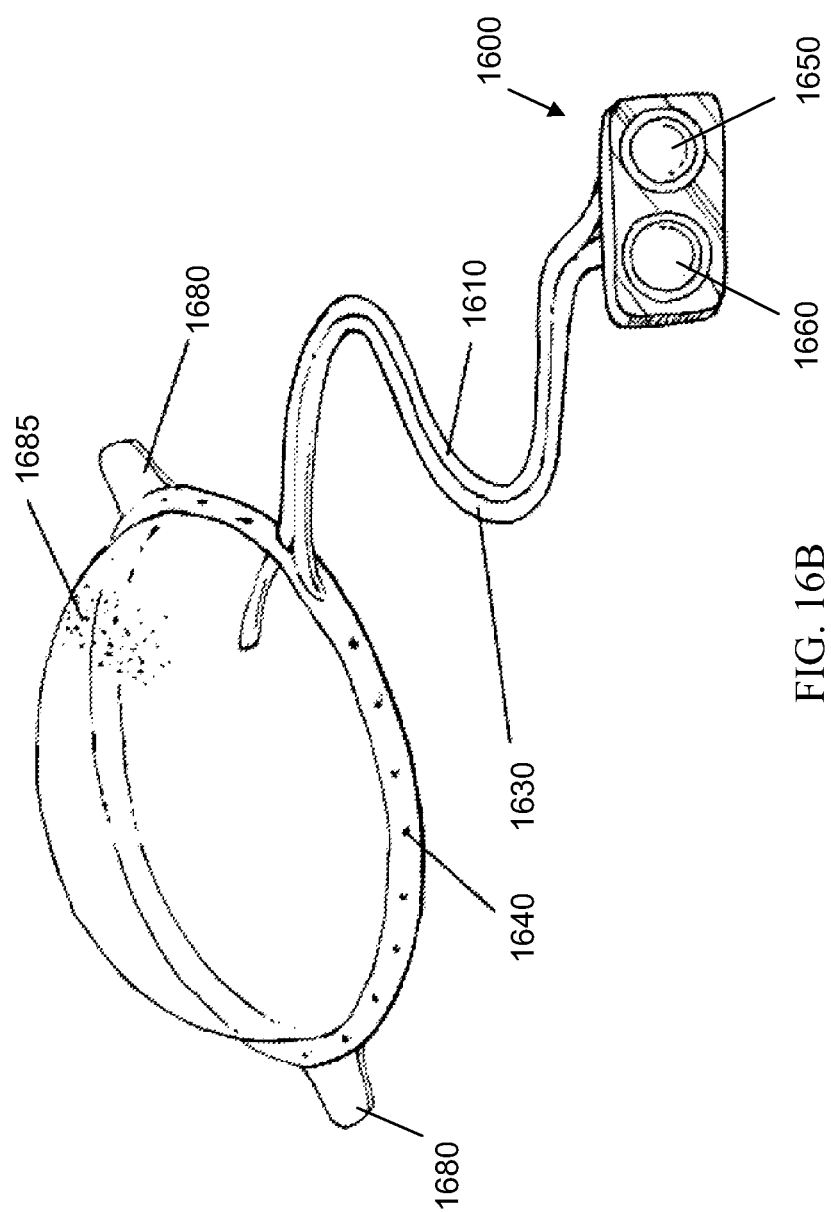
FIG. 16B shows an additional example of a dual remote port in accordance with aspects of the invention.

FIG. 16B shows an additional view of a dual remote port 1600 such as that described with respect to FIG. 16A. The dual remote port 1600 may have a first implant port 1650 fluidically connected to the interior of a tissue expander via an implant communication channel 1610. A second pocket port 1660 may be fluidically connected to a pocket channel system comprising a delivery canal 1640. The pocket channel system comprising the delivery canal 1640 may include one or more openings and may be in fluidic communication with an area surrounding the tissue expander, such as a pocket. One or more stability tabs 1680 may be provided.

The tissue expander may be coated with an antibiotic and/or antimicrobial coating 1685. In some embodiments, the tissue expander may have a dissolvable coating or cover. The dissolvable coating or cover may be used in combination with antibiotics or an antimicrobial coating, or may be used without the antibiotics or antimicrobial coating. Such coatings and/or covers may prevent the formation of a biofilm on the tissue expander. In some embodiments, portions or the entire surface of the tissue expander may be so coated or covered. In some embodiments, portions of the tissue expander may have a first type of coating and/or cover while other portions of the tissue expander may have a second type of coating and/or cover.

Figure 17:
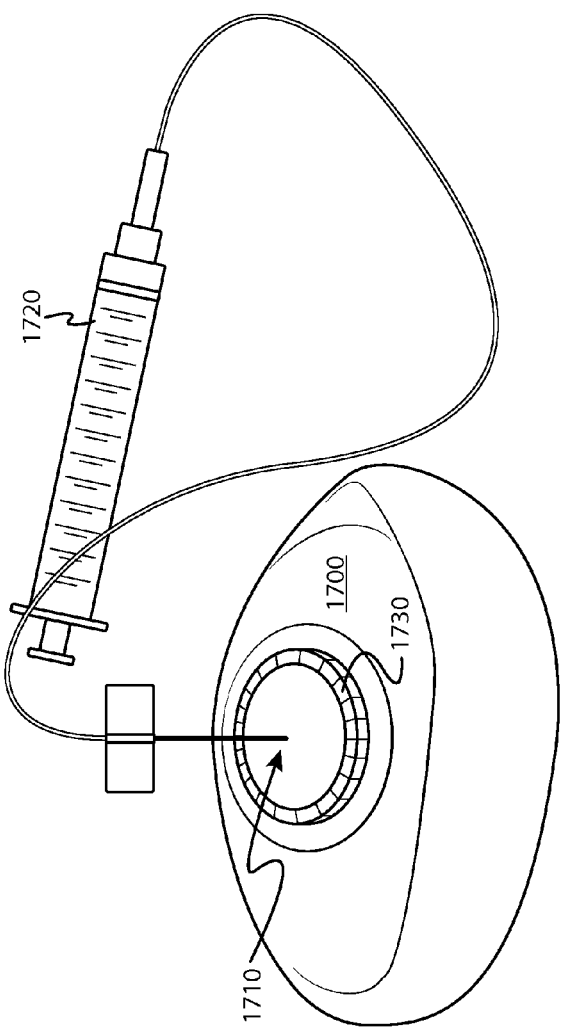
FIG. 17 shows a tissue expander with a dual integrated port in accordance with aspects of the invention.

FIG. 17 shows a tissue expander with a dual integrated port 1710. The tissue expander may include an implant shell 1700 and a dual integrated port 1710. A fluid delivery system, such as a needle and syringe 1720 may be utilized to provide one or more fluids to the dual integrated port 1710. The dual integrated port 1710 may be integral to the tissue expander implant shell 1700, or may be otherwise directly connected to or formed in or on the implant shell 1700.

In embodiments, the dual integrated port 1710 may have a top layer that is formed of a self-sealing material (also referred to herein as self-healing material). Thus, a needle may penetrate the top layer, but when the needle is removed, the material may self-seal to a fluid-tight state as before the needle penetration. A first plate formed of a sturdy material (such as metal) may be located within the dual integrated port underneath the top layer, and may be configured to catch the needle to prevent it from penetrating too deeply into the dual integrated port 1710. The first plate may have a second self-healing material around it within an interior of the dual integrated port 1710. An area 1730 can be provided for which the needle may be walked over and pushed through the second self-healing material layer past the first plate. A second plate may be provided beneath the first plate to catch the needle. Thus, if the needle penetrates the second self-healing material layer, it may be caught by the second plate and thus prevented from penetrating out of the dual integrated port 1710. In embodiments, and in contrast to the dual remote port of FIGS. 16A-B, the dual integrated port 1710 is formed integral with, or otherwise formed on or in, the implant shell 1700.

Figure 18:
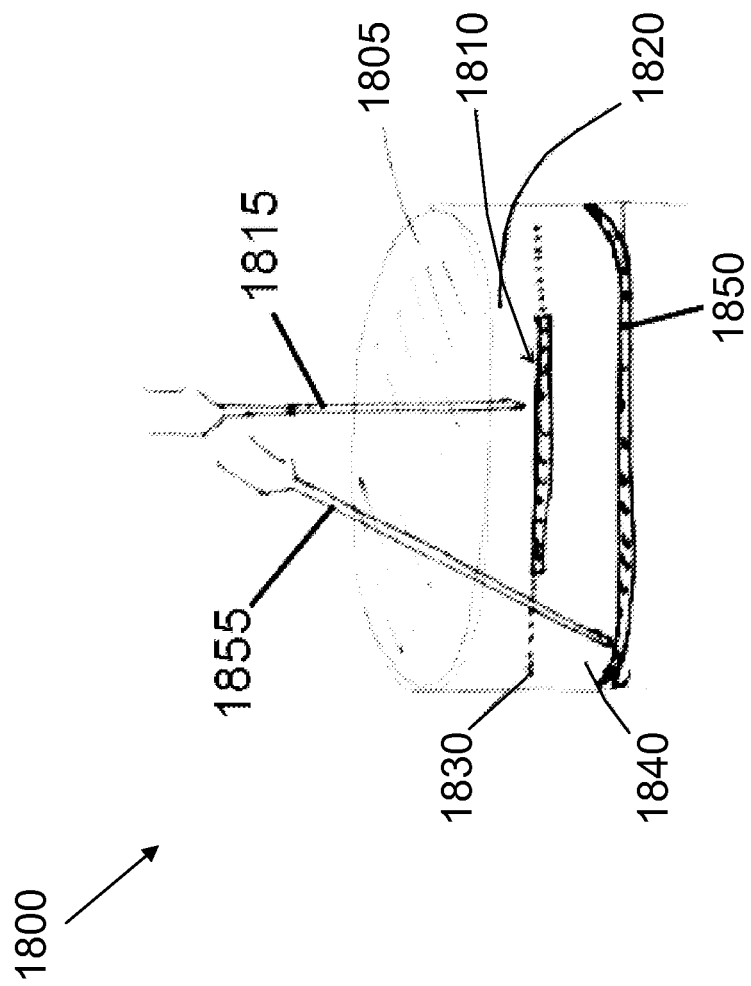
FIG. 18 shows a side view of a dual integrated port in accordance with aspects of the invention.

FIG. 18 shows a side view of a dual integrated port 1800, which may be similar in structure and/or functionality to dual integrated port 1710 described with respect to FIG. 17. In accordance with aspects of the invention, the dual integrated port 1800 may provide a user with selective fluid communication access to both an area internal to the tissue expander (e.g., for inflation and deflation of the tissue expander) and an external pocket surrounding the tissue expander (e.g., for injecting/extracting fluid to/from the pocket) through the same port, respectively and exclusively of one another.

In embodiments, the dual integrated port 1800 may have a first external layer 1805. The first external layer 1805 may be formed of a soft outer covering that is formed in an integral manner with, or otherwise formed on or in, the implant shell of the tissue expander. This first external layer 1805 may be a self-sealing material so when the first external layer 1805 is penetrated by a needle, it may self-seal once the needle is removed, preventing any fluid inside from escaping or any external fluid from entering.

In embodiments, the dual integrated port 1800 comprises a first plate 1810. The first plate 1810 may be formed of a sturdy material. For example, the first plate 1810 may be formed of a metal backing. Such metals may include but are not limited to steel, aluminum, silver, gold, copper, brass, titanium, or mixtures or alloys thereof. When the user inserts a needle 1815 into a central region of the dual integrated port 1800, the needle may hit the first plate 1810. When the user hits the first plate 1810 with the needle 1815, the user will know that the user is injecting a fluid into a first section 1820 of the dual integrated port 1800.

The first section 1820 of the dual integrated port 1800 may be in fluid communication with a first portion of the tissue expander. The first section 1820 of the dual integrated port 1800 may be connected to the first portion of the tissue expander via one or more communication channels, such as the communication channels described herein. In embodiments, the first section 1820 of the dual integrated port is in fluid communication with one or more cavities defined by the interior of the implant shell for inflation and deflation of the tissue expander. A first fluid (such as saline, air, or any other fluid) may be delivered via the needle into the first section 1820 and delivered to the inside cavity of the tissue expander. In embodiments, the first section may form an anterior lumen for the dual integrated port 1800. The anterior lumen may be in fluid communication with the inside cavity of the implant shell.

A second soft layer 1830 may be provided along the periphery of the first plate 1810. The second soft layer 1830 may also be formed of a self-sealing material. When a practitioner wants to access a second section 1840 of the dual integral port 1800, the practitioner may push the needle 1815 through the second soft layer 1830 until the needle 1815 hits a second plate 1850. Like the first plate 1810, the second plate 1850 may be formed of a sturdy material, such as a metal backing. In order to access the second section 1840, the needle 1815 may be angled as depicted by 1855 to push through to the second plate 1850. When the needle 1815 penetrates the first layer 1805 and hits the first plate 1810, the needle 1815 may be walked along the first plate 1810 until the practitioner feels a "step off" or "softness" and then pushes through the second soft layer 1830 through to the second plate 1850.

The second section 1840 of the dual integrated port 1800 may form a posterior lumen in fluid communication with a second portion of the tissue expander. The second section 1840 of the dual integrated port 1800 may be connected to the second portion of the tissue expander via one or more communication channels. In embodiments, the second portion of the tissue expander may be a channel system or delivery canal that may be in fluid communication with the pocket surrounding the tissue expander. A second fluid (such as medication, antibiotics, anti-microbial solution, or any other fluid) may be delivered via the needle to the second section 1840 and delivered to the pocket surrounding the tissue expander.

In alternate embodiments the first section 1820 may be in fluid communication with the pocket surrounding the tissue expander and the second section 1840 may be in fluid communication with the internal area of the tissue expander. In accordance with aspects of the invention the dual integrated port 1800 provides fluid communication access to two separate areas using a single needle stick of the patient. For example, in another embodiment, the first section 1820 may be in fluid communication with a first inflatable cavity within the implant shell, and the second section 1840 may be in fluid communication with a second inflatable cavity within the same implant shell, wherein the first inflatable cavity and the second inflatable cavity are not in fluid communication with each other. In such a configuration, the dual integrated port 1800 could be used to inflate/deflate the first cavity and separately inflate/deflate the second cavity with only a single insertion of the needle into the patient.

Figure 19:
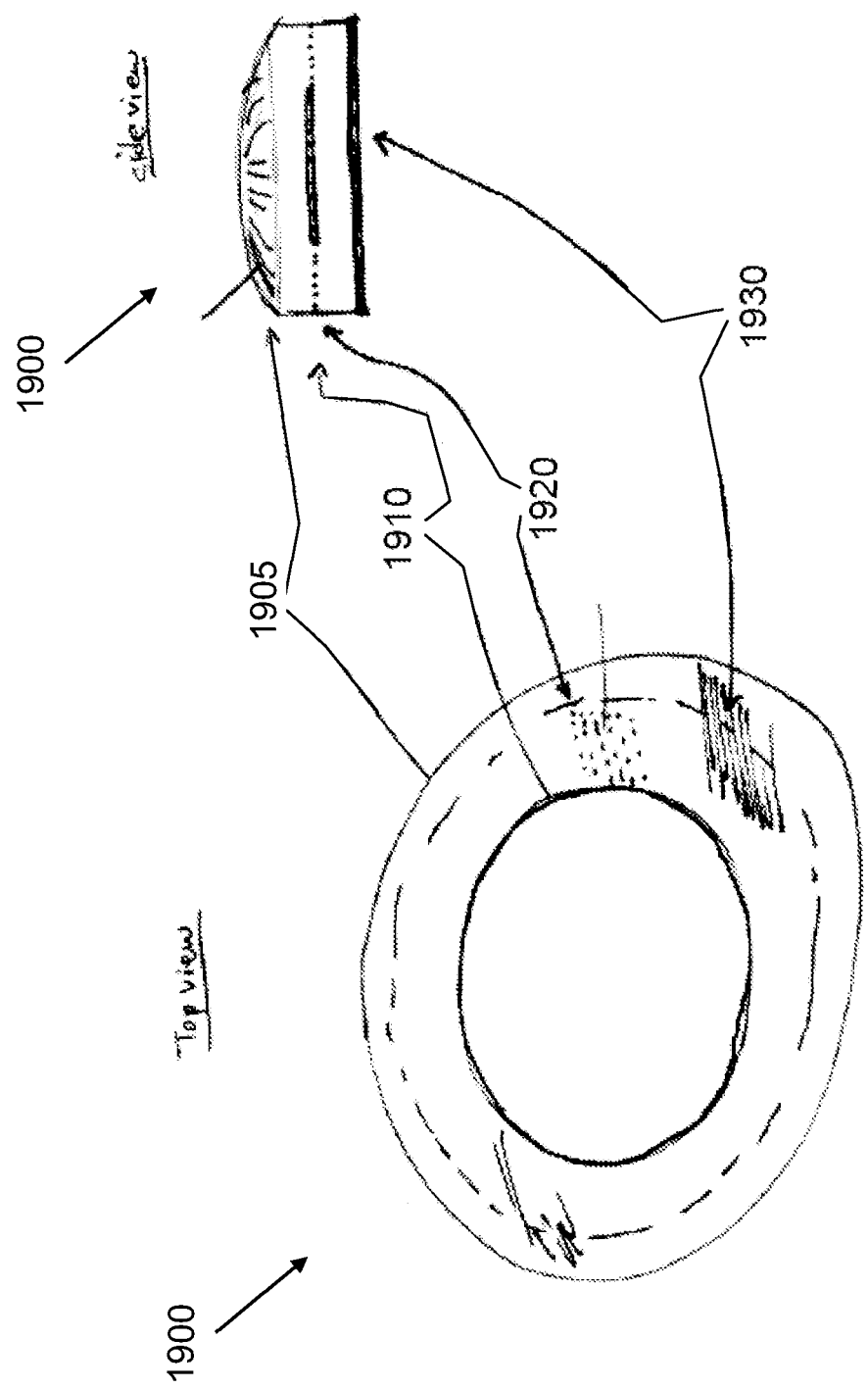
FIG. 19 shows a top view and side view of a dual integrated port in accordance with aspects of the invention.

FIG. 19 shows a top view and side view of a dual integrated port 1900, which may be similar in structure and/or functionality to dual integrated ports 1800 and 1710. A port top 1905 may be provided, which may be formed of a self-sealing material. A first plate 1910 maybe provided beneath the port top 1905. A second self-sealing material layer 1920 may be provided on the same level as the first plate 1910 and may surround the periphery of the first plate 1910. It may be advantageous to have the second self-sealing material layer 1920 at the same level as the first plate 1910 so that the second self-sealing layer 1920 may provide support to the first plate 1910. In other embodiments, the second self-sealing material layer 1920 may be provided beneath the first plate 1910 and need not be at the same level. A second plate 1930 may be provided beneath the first plate 1910 and second self-sealing layer 1920. The second plate 1930 may be deeper than the first plate 1910 and/or the second self-sealing layer 1920.

Although the first plate 1910 is shown as a circular plate at the center of the dual integrated port 1900, the first plate 1910 may have different shapes or placement. For example, the first plate 1910 may be offset to a side of the port, or maybe surrounding a central region of the dual integrated port 1900. For example, the first plate 1910 may be a half-circle or any part of a circle, a donut, an ellipse, a triangle, a rectangle, a pentagon, hexagon, an octagon or any other shape.

Although two sections are shown within the dual access ports 1710, 1800, and 1900, any number of sections may be provided in a dual access port in accordance with aspects of the invention. In some examples, three, four or more sections may be provided in a dual access port. In such situations, additional plates and additional soft layers may be provided, that may enable a practitioner to access the desired section of the access port. In one example, circular metal plates may be provided, so that for each level deeper, they have a progressively increasing area, like a tiered cake. In another example, the metal plates may have a staggered configuration. A needle may penetrate increasingly deeper to access various sections of the access port, to deliver and/or retrieve different fluids to different parts of the tissue expander or surrounding area.

Figure 20:
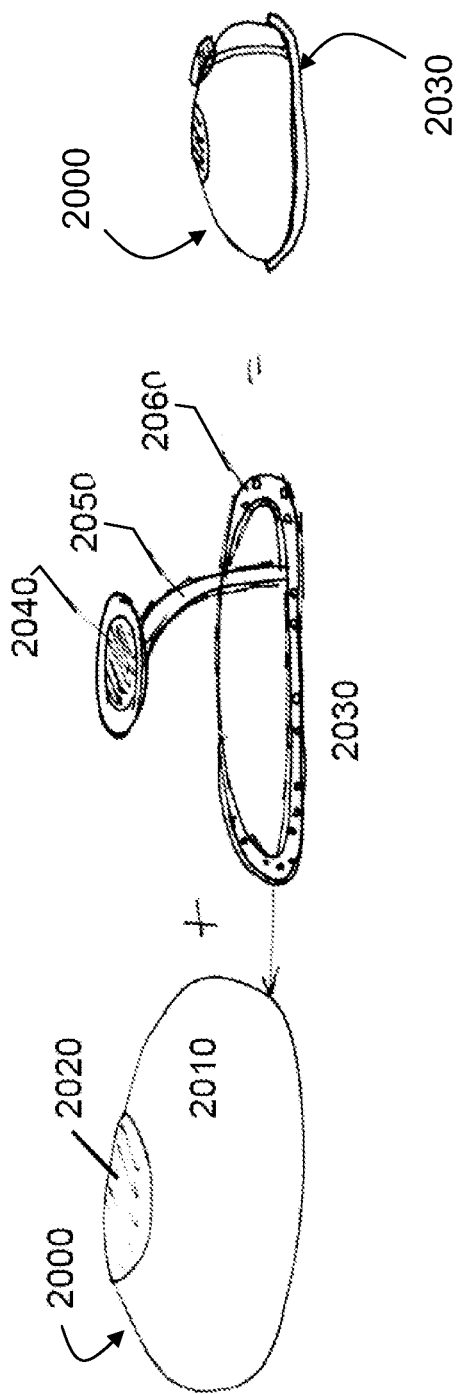
FIG. 20 shows an example of a tissue expander with separable components in accordance with aspects of the invention.

The dual access port in accordance with aspects of the invention may be integrated into the tissue expander. In other embodiments, the dual access port with the multiple layers described may also be provided as a remote port. In some instances, a plurality of dual access ports may be provided. For example, two dual access ports with two or more internal lumens may be provided integral and/or remote to the tissue expander. This may provide flexibility if additional fluids are utilized or sections are being accessed. Magnetic polarity and/or placement may be utilized to differentiate between a plurality of dual access ports. Stability Tabs
Separable Components FIG. 20 shows an example of a tissue expander with separable components in accordance with aspects of the invention. In one example, a tissue expander 2000 may be provided, the tissue expander 2000 comprising an implant shell 2010 and an implant port 2020 for inflating/deflating a cavity defined by the implant shell 2010. In embodiments, a drainage/delivery system 2030 may be added to the tissue expander 2000. The drainage/delivery system 2030 may include a pocket port 2040, a communication channel 2050, and a delivery canal 2060. The drainage/delivery system 2030 may have various shapes, configurations, or features as described elsewhere herein. In particular, the delivery canal 2060, pocket port 2040, and communication channel 2050 may be similar in structure and/or functionality to other delivery canals, pocket ports, and communication channels described herein with respect to other figures. For example, the pocket port 2040 may be an integral pocket port or may be a remote pocket port with need not contact the implant wall.

The drainage/delivery system 2030 may be added to the tissue expander 2000 by being clipped onto, or otherwise connected to, the standard tissue expander. In other embodiments, the drainage/delivery system 2030 may be glued or otherwise adhered to the standard tissue expander. In some instances, the drainage/delivery system 2030 and the tissue expander 2000 may be heat welded together. In other examples, the drainage/delivery system 2030 and the tissue expander 2000 may be mechanically connected via locking components, fasteners, grooves, sliding components, clamping components, ties, or any other parts.

In accordance with aspects of the invention, this configuration may enable the delivery/drainage system 2030 to be made independently of a tissue expander 2000 and supplied separately from the tissue expander 2000 as a kit or aftermarket assembly. The drainage/delivery system 2030 may then be added post-production to the tissue expander 2000. The drainage/delivery system 2030 may be bonded by adhesive to the tissue expander 2000 and still perform the same function as if the delivery/drainage system 2030 were made integrated with the tissue expander 2000. An advantage of this lies in that the delivery/drainage system 2030 may be added to a production line tissue expander 2000 without altering the tooling for manufacturing the tissue expander 2000. This configuration provides an option for a company with potentially lower production costs. This configuration also enables a practitioner or production entity to utilize pre-existing tissue expanders and subsequently attach the delivery/drainage system 2030 when desirable.
Materials Any parts of a tissue expansion system as described may utilize any material known or later developed in the art. Preferably, the materials used may include biocompatible materials.

Figure 21A:
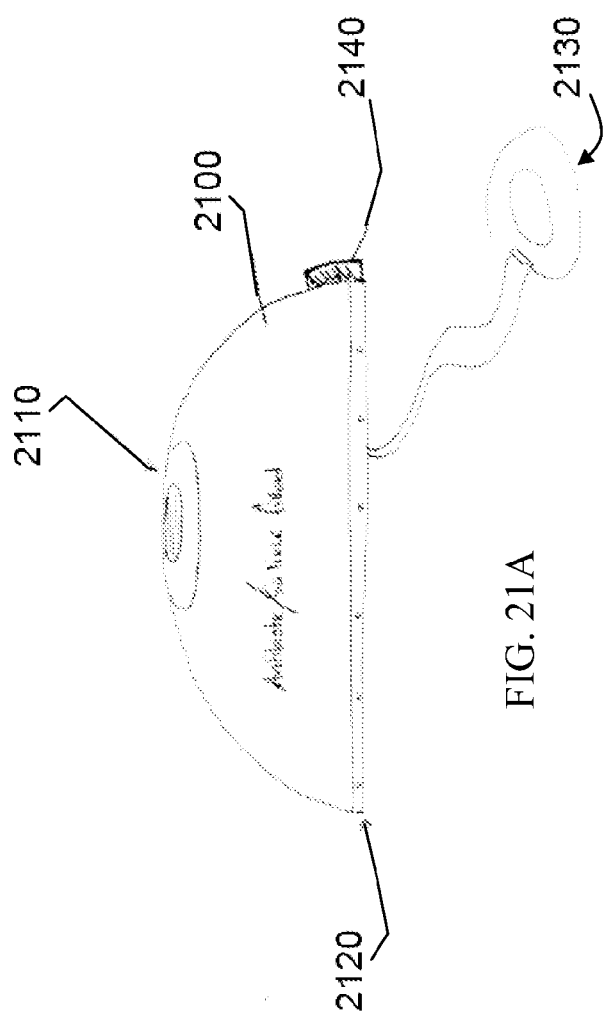
FIGS. 21A and 21B show a tissue expander formed of various materials in accordance with aspects of the invention.

FIG. 21A shows a tissue expander formed of various materials. In embodiments, the tissue expander may have a covering 2100, an access port 2110, a delivery canal system 2120, and a pocket port 2130. The pocket port 2130 may or may not be a remote port. The pocket port 2130 may be built into the main implant next to the implant port. Alternatively, the pocket port 2130 can be remote to ease access for placement of fluids.

The covering 2100 may have a coating. For example, the covering 2100 may be coated with an antibiotic material which may leach out. In other examples, the covering 2100 may include antimicrobial or any other type of medication or treatment. In some embodiments, the covering 2100 may include an outer layer 2140 which may be composed of a dissolving material. The dissolving material may be impregnated with antibiotics, antimicrobial solution, silver, or any other medication or treatment, so that when it slowly dissolves, it may release the medication or treatment. The covering 2100 may be formed of a pliable, amorphous material, such as caprolactone or L-lactide. The covering 2100 would be formed of a material that is sufficiently malleable to allow expansion, along with expansion of the tissue expander.

Figure 21B:
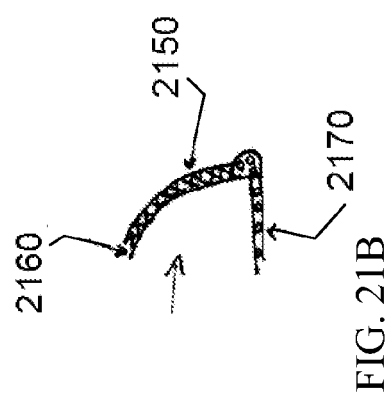

As depicted in FIG. 21B, a covering 2150, which may be similar to covering 2100, may be bonded to the implant shell 2160 of the implant and impregnated with antibiotics, silver, or other treatment. In some instances, slowly over a time period, the covering 2150 may dissolve, leaving a bare shell. The time period may vary, including but limited to about 1 day, 1 week, 2 weeks, 1 month, 2 months, 3 months, 4 months, 6 months, or 1 year or more or less. The covering 2150 may give off antibiotics, silver, or any other treatment over time. This may assist with preventing or treating infection.

Having an outside bonded shell that may dissolve over time may also help prevent a biofilm from surviving. This may occur from an antibiotic standpoint as well as by removing the biofilm "floor" as it may dissolve away, such as a sand castle eroding in water at the beach.

The tissue expander may include one or more channels 2170, which may be similar in structure and/or functionality to other channels and delivery canals described herein. The channels 2170 may or may not include a dissolvable covering or coatings, as described herein.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A tissue expander, comprising:
   an implant shell defining an internal cavity configured to contain a fluid;
   an implant port providing fluidic access to the internal cavity of the implant shell for selectively inflating and deflating the implant shell;
   a delivery system contacting the implant shell, wherein the delivery system is in fluidic communication with an area at an exterior of the tissue expander; and
   a pocket port providing fluidic access to the delivery system,
   wherein:

the implant port and the pocket port are integrated in the implant shell;

the implant port and pocket port are at different locations on the implant shell with a portion of the implant shell extending between the implant port and pocket port;

the delivery system includes a delivery canal; and a communication channel extends between the pocket port and the delivery canal and places the pocket port in fluid communication with the delivery canal.

2. The tissue expander of claim 1, wherein the delivery system includes the delivery canal encircling at least a portion of a circumference of the implant shell on a posterior side of the tissue expander.

3. The tissue expander of claim 2, wherein the delivery canal comprises a plurality of openings that place an interior of the delivery canal in fluidic communication with the area at the exterior of the tissue expander.

4. The tissue expander of claim 3, wherein the delivery system, including the delivery canal, is fluidically isolated from the internal cavity of the implant shell.

5. The tissue expander of claim 2, wherein:
the delivery system further comprises an auxiliary delivery canal at an anterior side of the tissue expander;
the auxiliary delivery canal comprises a plurality of holes; and
the delivery canal and the auxiliary delivery canal are in fluidic communication.

6. The tissue expander of claim 2, wherein the delivery canal is more rigid than the implant shell.

7. The tissue expander of claim 2, wherein the pocket port provides fluidic access to the delivery system via the communication channel.

8. The tissue expander of claim 1, wherein:
the delivery system comprises a double-wall delivery region;
the implant shell is a first wall of the double-wall delivery region; and
a second wall of the double-wall delivery region comprises a plurality of holes that place an interior of the double-wall delivery region in fluidic communication with the area at the exterior of the tissue expander.

9. The tissue expander of claim 1, further comprising a coating on an exterior surface of the tissue expander, wherein the coating is configured to dissolve inside a patient body.

10. The tissue expander of claim 1, wherein:
the implant port provides selective fluidic access to the internal cavity for at least one of: inflating and deflating the tissue expander; and
the pocket port provides selective fluidic access to the delivery system for at least one of: injecting a fluid into the area at the exterior of the tissue expander, and extracting fluid from the area at the exterior of the tissue expander.

11. The tissue expander of claim 1, wherein the communication channel is internal to the implant shell.

12. The tissue expander of claim 1, wherein the communication channel is built into an internal surface of the implant shell.

13. The tissue expander of claim 1 further comprising stability tabs on opposing sides of the tissue expander.

14. The tissue expander of claim 1, wherein the pocket port includes a penetrating surface of self-healing material and a sturdy material on an other side of the penetrating surface.

15. The tissue expander of claim 1, wherein:
the delivery canal is made from a different material than the implant shell; and
the delivery canal includes reinforcing members to make it more rigid than the implant shell.

16. The tissue expander of claim 1, further comprising stability tabs that are configured to be sewn to a portion of a patient body, and wherein:
the communication channel is in the internal cavity of the implant shell;
the pocket port includes a penetrating surface of self-healing material and a sturdy material on an other side of the penetrating surface; and
the delivery canal is more rigid than the implant shell.

17. A method for tissue expansion using the tissue expander recited in claim 1, the method comprising:
providing a first fluid via the implant port to the implant shell configured to contain the first fluid within, wherein the implant port is integral to the implant shell; and
providing a second fluid via the pocket port to the delivery canal in contact with the implant shell, thereby causing the second fluid to extrude from the delivery canal to an area outside the implant shell.

18. A tissue expander, comprising:
an implant shell defining an internal cavity configured to contain a fluid;
an implant port providing fluidic access to the internal cavity for selectively inflating and deflating the implant shell;
a delivery canal contacting at least a portion of the implant shell and comprising a plurality of openings that place an interior of the deliver canal in fluidic communication with an area at an exterior of the tissue expander;
a communication channel connected to and in fluidic communication with the delivery canal; and
a pocket port connected to and in fluidic communication with the communication channel, wherein:
the implant port provides selective fluidic communication with the internal cavity exclusive of the delivery canal;
the pocket port provides selective fluid communication with the delivery canal exclusive of the internal cavity;
the pocket port, the communication channel, and the delivery canal are configured for at least one of: injecting a fluid into the area at the exterior of the tissue expander, and extracting fluid from the area at the exterior of the tissue expander; and
the delivery canal is more rigid than the implant shell,
further comprising stability tabs extending outward from the implant shell, and wherein:
the implant port and the pocket port are integrated in the implant shell;
the implant port and pocket port are at different locations on the implant shell with a portion of the implant shell extending between the implant port and pocket port; and
the communication channel is in the internal cavity of the implant shell.

* * * * *